United States Patent
Omura et al.

(10) Patent No.: US 6,586,200 B2
(45) Date of Patent: Jul. 1, 2003

(54) METHOD FOR DETECTING SUBSTANCES INHIBITING THE BACTERIAL TYPE III SECRETION MECHANISM AND FUNCTION OF SECRETORY PROTEINS THEREOF

(75) Inventors: Satoshi Omura, Tokyo (JP); Akio Abe, Tokyo (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 09/937,832

(22) PCT Filed: Jan. 22, 2001

(86) PCT No.: PCT/JP01/00377

§ 371 (c)(1),
(2), (4) Date: May 21, 2002

(87) PCT Pub. No.: WO02/057760

PCT Pub. Date: Jul. 25, 2002

(65) Prior Publication Data

US 2002/0192740 A1 Dec. 19, 2002

(51) Int. Cl.[7] ............................ C12Q 1/04; C12Q 1/18; C12Q 1/00
(52) U.S. Cl. .................... 435/34; 435/32; 435/7.25; 435/4
(58) Field of Search ..................... 435/34, 32, 7.25, 435/4

(56) References Cited

U.S. PATENT DOCUMENTS 6,136,542 A   10/2000   Demers et al. ................ 435/6

FOREIGN PATENT DOCUMENTS

| WO | WO 99/45136 | | 9/1999 |
|---|---|---|---|
| WO | WO 200257760 | * | 7/2002 |

OTHER PUBLICATIONS

J. Warawa et al., Type III Secretion–Dependent Hemolytic Activity of Enteropathogenic *Escherichia coli*, *Infection and Immunity*, Oct. 1999, p. 5538–5540.

Y. Li et al, Human Response to *Escherichia coli* O157:H7 Infection: Antibodies to Secreted Virulence Factors, *Infection and Immunity*, Sep. 2000, p. 5090–5095.

A. Blocker et al., The Tripartite Type III Secretion of *Shigell flexneri* Inserts IpAb and IpaC Into Host Membranes, *Journal of Cell Biology*, vol. 147, No. 3, Nov. 1999 p. 683–693.

T. K. McDaniel et al., A Cloned Phathogenicity Island from Enteropathogenic *Escherichia coli*, Confers the Attaching and Effacing Phenotype on *E. coli* K–12, *Molecular Microbiology* (1997) vol. 12, No. 2, p. 399–407.

(List continued on next page.)

Primary Examiner—Louise N. Leary
(74) Attorney, Agent, or Firm—Young & Thompson

(57) ABSTRACT

The present invention relates to a method for detecting substances specifically inhibiting a type III secretion mechanism and functions of the type III secretory proteins, within short time and large amounts thereof, without depending upon animal infectious experiments. Namely it relates to the method for detection of a type III secretory mechanism inhibitor comprising mixing a bacterium having the type III secretory mechanism and an erythrocyte suspension, adding the type III secretory mechanism inhibitor thereto, and detecting changes in the thus formed hemolytic activity. The method for detecting substances can be treated large amount of samples within short time by exhibiting the substances inhibiting the type III secretion mechanism or the functions of the type III secretory proteins as numerical index of the hemolytic activity of erythrocytes. Consequently, the present invention is useful for development of drugs.

10 Claims, 12 Drawing Sheets

OTHER PUBLICATIONS

A. Abe et al., Enteropathogenic *Escherichia coli* Translocated Intimin Receptor, TIR, Requires a Specific Chaperone for Stable Secretion, *Molecular Microbiology*, (1999) vol. 33, No. 6, p 1162–1175.

M.S. Donnenberg et al., Construction of an eae Deletion Mutant of Enteropathogenic *Escherichia coli* by Using a Positive–Selection Suicide Vector, *Infection and Immunity*, (1991), p. 4310–4317.

R.Simon et al., A Broad Host Range Mobilization System and for In Vivo Genetic Engineering: Transposon Mutagenesis in Gram Negative Bacteria, *Bio/technology*, Nov. 1983, p. 784–791.

K.G.Jarvis et al., Enteropathogenic *Escherichia coli*, Contains a Putative Type III Secretion System Ecessary fo the Export of Proteins Involved in Attaching and Effacing Lesion Formation, *Proc. Ntl. Acad. Sci*, Aug. 1995, p. 7996–8000.

B.Kenny et al., ESPA, A Protein Secteted by Enteropathogenic *Escherichia coli*, is Required to Induce Signals in Epithelial Cells, *Molecular Microbiology*, (1996) p. 313–323.

M.S. Donnenberg et al, A Second Chromosomal Gene Necessary for Intimate Attachment of Enteropathogenic *Escherichia coli* to Epithelial Cells, *Journal of Bacteriology*, 1993, vol. 175, No. 15, p. 4670–4680.

L. Lai et al., A Third Secreted Protein Tha Tis Encoded by the Enterophogenic *Escherichia coli* Pathogenicity Island is Required for Transduction of Signals and for Attaching and Effacing Activities in Host Cells, *Infection and Immunity*, Jun. 1997, p. 2211–2217.

C.Sasakawa et al., Molecular Alteration of the 140–Megadalton Plasmid Associated with Loss of Virulence and Congo Red Binding Activity in *Shigella flexneri*, *Infection and Immunity*, Feb. 1986, p. 470–475.

J.E.Galan et al., Molecular and Functional Characterization of the Salmonella Invasion Gene invA: Homology of invA to Members of a New Protein Family, *Journal of Bacteriology*, Jul. 1992, p. 4338–4349.

O.Marches et al., Role of Tir and Intimin in the Virulences of Rabbit Enteropathogenic *Escherichia coli*, Serotype O103:H2 *Infection and Immunity*, Apr. 2000, p. 2171–2182.

* cited by examiner

5'-GC<u>GTCGAC</u>GTACTTATGCGCTTCTGGCAAA-3'
   Sal I
5'-GC<u>GAGCTC</u>CAACGTATAAAAAGGCGATTC-3'
   Sac I

5'-CG<u>GGATCC</u>TTACTCTGCAAACCATAAGTTT-3'
   BamH I
5'-CG<u>GGATCC</u>GTGGGCCATACCTGTGTTATG-3'
   BamH I

5'-GC<u>GTCGAC</u>ATGATTTCAGAGCATGATTCTG-3'
    Sal I

5'-GC<u>GAGCTC</u>TCAGGCAACCACTTTGAATAGG-3'
    Sac I

5'-GA<u>AGATCT</u>TTAAGAAAGCGTGGATTGAGG-3'
    Bgl II

5'-GA<u>AGATCT</u>GTGTGCTGGTCGTCACAACGTC-3'
    Bgl II

5'-GC<u>GTCGAC</u>ATCGATTGTCGAAGATAAACAT-3'
    Sal I
5'-GC<u>GAGCTC</u>AGAGGGCGTCACTAATGAGTGA-3'
    Sac I

5'-GA<u>AGATCT</u>TTAGCTACTCTGAACGTCAGCA-3'
    Bgl II
5'-GA<u>AGATCT</u>ACAAGAATGCGAAAGCTCAACT-3'
    Bgl II

5'-GC<u>GTCGAC</u>ATGAATACTATCGATAATAACAA-3'
    Sal I
5'-GC<u>GAGCTC</u>TTACCCAGCTAAGCGAGCCGCT-3'
    Sac I

5'-GA<u>AGATCT</u>TTATGCAATACCTTCGGAAGCC-3'
    Bgl II
5'-GA<u>AGATCT</u>CAGCAGATGATGCAGCTGGCGC-3'
    Bgl II

5'-GC<u>GTCGAC</u>ATGCTTAATGTAAATAACGATA-3'
    Sal I
5'-GC<u>GAGCTC</u>TTAAACTCGACCGCTGACAATA-3'
    Sac I

5'-CG<u>GGATCC</u>TTAAGTTGCTGCAACCCCTAAC-3'
    BamH I
5'-CG<u>GGATCC</u>TTGCAGCTATTTTTAACCCGG-3'
    BamH I

5'-CC<u>CCCGGG</u>ATGTTGCAAAAGCAATTTTGCA-3'
      <u>Sma I</u>
5'-GC<u>TCTAGA</u>TTAAGCTCGAATGTTACCAGCA-3'
     <u>Xba I</u>

5'-CG<u>GGATCC</u>TTAGGCACCGATACCCGTTATA-3'
    <u>BamH I</u>
5'-CG<u>GGATCC</u>AAACGCATTCAGGGATTAGCGA-3'
    <u>BamH I</u>

5'-GC<u>GTCGAC</u>GTGCTGCTTTCTCTACTTAACA-3'
   Sal I
5'-GC<u>GAGCTC</u>TTATATTGTTTTTATAACATTC-3'
   Sac I

5'-GC<u>TCTAGA</u>TTATTCCTCAATACTGAGCGGC-3'
   Xba I
5'-GC<u>TCTAGA</u>AAGGGTCGTCGTTAGGACTGAT-3'
   Xba I

5'-CC<u>CCCGGG</u>ATGCGTCAGTACCACTACATCA-3'
    <u>Sma I</u>
5'-GC<u>GAGCTC</u>TTAGGATTCGGGTCCGATGATT-3'
    <u>Sac I</u>

5'-GA<u>AGATCT</u>TTAGCTCTTGCGTCTGCCCTC-3'
    <u>Bgl II</u>
5'-GA<u>AGATCT</u>TCGTTTGCGCGACCAGCGACAA-3'
    <u>Bgl II</u>

SEQUENCE LISTING

<160> NUMBER OF SEQ ID NOS: 32

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 1
gcgtcgacgt acttatgcgc ttctggcaaa                30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
gcgagctcca acgtataaaa aaggcgattc                30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 3
cgggatcctt actctgcaaa ccataagttt                30

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 4
cgggatccgt gggccatacc tgtgttatg                 29

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 5
gcgtcgacat gatttcagag catgattctg                30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6
gcgagctctc aggcaaccac tttgaatagg                30

<210> SEQ ID NO 7
<211> LENGTH: 29

```
<212> TYPE: DNA
<213> ORGANISM: Artificial Sequence
<220> FEATURE:
<223> OTHER INFORMATION: Description of Artificial Sequence: Primer

<400> SEQUENCE: 7
gaagatcttt aagaaagcgt ggattgagg                                29

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
gaagatctgt gtgctggtcg tcacaacgtc                               30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
gcgtcgacat cgattgtcga agataaacat                               30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
gcgagctcag agggcgtcac taatgagtga                               30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
gaagatcttt agctactctg aacgtcagca                               30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 12
gaagatctac aagaatgcga aagctcaact                               30

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 13
```

```
gcgtcgacat gaatactatc gataataaca a                                    31

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
gcgagctctt acccagctaa gcgagccgct                                       30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 15
gaagatcttt atgcaatacc ttcggaagcc                                       30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 16
gaagatctca gcagatgatg cagctggcgc                                       30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 17
gcgtcgacat gcttaatgta aataacgata                                       30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 18
gcgagctctt aaactcgacc gctgacaata                                       30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 19
cgggatcctt aagttgctgc aaccccctaac                                      30

<210> SEQ ID NO 20
<211> LENGTH: 29
<212> TYPE: DNA
<213> ORGANISM: Artificial Sequence
```

```
<220> FEATURE:
<223> OTHER INFORMATION: Description of Artificial Sequence: Primer

<400> SEQUENCE: 20
cgggatcctt gcagctattt ttaacccgg                                      29

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 21
cccccgggat gttgcaaaag caattttgca                                     30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 22
gctctagatt aagctcgaat gttaccagca                                     30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 23
cgggatcctt aggcaccgat acccgttata                                     30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 24
cgggatccaa acgcattcag ggattagcga                                     30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 25
gcgtcgacgt gctgctttct ctacttaaca                                     30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 26
gcgagctctt atattgtttt tataacattc                                     30
```

-continued

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 27
gctctagatt attcctcaat actgagcggc                                30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 28
gctctagaaa gggtcgtcgt taggactgat                                30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 29
cccccgggat gcgtcagtac cactacatca                                30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 30
gcgagctctt aggattcggg tccgatgatt                                30

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 31
gaagatcttt agctcttgcg tctgccctc                                 29

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 32
gaagatcttc gtttgcgcga ccagcgacaa                                30

METHOD FOR DETECTING SUBSTANCES INHIBITING THE BACTERIAL TYPE III SECRETION MECHANISM AND FUNCTION OF SECRETORY PROTEINS THEREOF

TECHNICAL FIELD

The present invention relates to a method for detecting substances inhibiting the type III secretion mechanism, which is highly conserved in bacteria belonging to, for example, genus Salmonella, genus Yersinia, genus Pseudomonas, Shigella, Enteropathogenic E. coli, Enterohaemorrhagic E. coli or genus Bordetella, and inhibiting functions of secretory proteins, within short time and large amounts thereof.

BACKGROUND ART AND PRIOR ART

Type III secretion mechanism, which functions to release bacterial pathogenic factors extracellularly, is highly conserved, for example, in genus Salmonella, genus Yersinia, genus Pseudomonas, Shigella, Enteropathogenic E. coli (hereinafter sometimes abbreviated as EPEC), Enterohaemorrhagic E. coli and genus Bordetella (Microbiology and Molecular Biology Reviews, June, 1998, p. 381).

It is known that bacteria, which conserves type III secretion mechanism hereinabove, release pathogenic factors extracellularly and a part of the released pathogenic factors was translocated into host cells (Microbiology and Molecular Biology Reviews, June, 1998, p. 389). The translocated pathogenic factors in the host cells are largely involved in pathogenicity of bacteria (Microbiology and Molecular Biology Reviews, June, 1998, p. 382-).

It ha demonstrated by in vivo infection experiments in rabbits (J. Exp. Med. 188(10), 1907–1916, Nov. 16, 1998) and infection tests with human volunteers (Infection and Immunity, June 2000, 3688–3695) that EPEC strain, which defects proteins secreted from the type III secretion mechanism (hereinafter sometimes designates as type III secreted protein), greatly decreased virulence. According to these facts, substances which inhibit the type III secretion mechanism and functions of the secretory proteins are expected their effects as new drugs for treatment and prevention of infectious diseases.

However, no methods for detecting substances which inhibit bacterial type III secretion mechanism have been established, furthermore at present, methods for detection based on antimicrobial activity have been mainstream. Methods for detecting substances having antimicrobial activities, i.e. antibiotic activities, have performed mainly by bioassay. The bioassay includes diffusion method (Microbiological Medicinal Chemistry, Rev. 3rd Ed., Nankodo Publ., Ed. Ohmura, Statoshi). When filter papers containing antibiotics are placed on agar plates containing test microorganisms, the antibiotics diffuse into the agar and inhibitory zone against growth of test microorganisms is observed as transparent zone. The detection method includes calculation of antibiotic potency from relationship between diameters of inhibitory zones and concentration of antibiotics.

Since the diffusion method is simple in operation and large numbers of samples can be treated within short time, it has widely used for detection of antibiotics. However, substances obtained by such method have bactericidal action against not only target microbes but also normal enterobacterial flora, as a result replacement of bacteria and multidrug resistant strains have appeared and at present various problems occur. Consequently, there are problems to apply such the test method for detecting substances which inhibit the bacterial type III secretion. From these facts, methods for detecting substances specifically inhibiting the type III secretion mechanism and the type III secreted protein secreted therefrom have not been established. Consequently, detection of substances, which inhibit the type III secretion mechanism and functions of the type III secretory protein secreted therefrom, have to rely upon experimental animal infective tests. As a result, complex operations have to be required and treatments of large numbers of test samples within short time were difficult.

We have studied that ideas for establishment of simple methods for detecting large amount of substances, which specifically inhibit the type III secretion mechanism and the functions of the type III secreted proteins secreted therefrom within short time, would be very important for development and evaluation of pharmaceutical product targeting the type III secretion mechanism. As a result, we have found novel detection methods without relying upon the experimental tests of animal infection.

An object of the present invention is to provide a method for detecting substances inhibiting the bacterial type III secretion mechanism and the functions of type III secreted proteins secreted therefrom wherein large numbers of the substances specifically inhibiting the bacterial type III secretion mechanism and the functions of the type III secreted proteins secreted therefrom can be detected within short time.

Another object of the present invention is to provide the method for detecting substances inhibiting function of the bacterial type III secretion mechanism and the type III secreted protein secreted therefrom wherein the substances inhibiting the bacterial type III secretion mechanism and the function of the type III secreted proteins secreted therefrom are expressed numerically as an index of the hemolytic activity of erythrocytes and as a result, large numbers of samples can be treated within short time.

DISCLOSURE OF INVENTION

When bacteria containing the type III secretion mechanism contacted with erythrocyte, hemolytic activity is induced. It has demonstrated that this hemolytic activity was dependent on an action of the type III secreted proteins on the erythrocytes (Infect. Immun. 67, 5538–5540, 1999). The present invention has completed by observing hemolytic activity induced bacteria containing the type III secretory mechanism. Consequently, the present invention is characterized by the inhibition of hemolytic activity by an addition of substances which inhibit the type III secretion mechanism.

The present invention relates to a method for detecting substances, which inhibit the type III secretion mechanism and the function of the type III secreted proteins secreted therefrom, by employing the hemolytic activity of erythrocytes as an index. The present invention relates to the method for detecting substances which inhibit bacterial type III secretion mechanism comprising mixing the bacteria containing the type III secretion mechanism and erythrocytes suspension, adding the substance which inhibits the type III secretion mechanism and detecting the detectable changes of the generated hemolytic activity. The present invention further relates to the method for detecting substances, which inhibit functions of the secreted proteins of the type III secretion mechanism, comprising mixing the bacteria containing the type III secretion mechanism and erythrocytes suspension, adding the substance, which inhibits the functions of the proteins secreted by an action of the type III secretion mechanism, and detecting the detectable changes of the generated hemolytic activity. Further, the present invention relates to the method for detection wherein the hemolytic activity is detected by colorimetry.

Test microorganisms for inducing hemolytic activities used in the present invention include any bacteria containing the type III secretion mechanism. Examples of bacteria used are, for example, genus Salmonella, genus Yersinia, genus Pseudomonas, Shigella, Enteropathogenic *E. coli*, Enterohaemorrhagic *E. coli* and genus Bordetella. In addition to these bacteria, recombinant bacteria, in which DNA regions including gene group, designated as LEE, DNA sequence of 35.4 kbp, coding the type III secretion mechanism and secreted proteins therefrom are artificially integrated into the other bacteria (Molecular Micro. 27, 399–407, 1997) and the similar recombinant bacteria are also included in the present invention.

Growth of test microorganisms is preferably performed in a relatively low nutritional medium such as M9 medium rather than in nutrient rich medium. Culture condition of the test microorganisms is preferably at 37° C., and the standing culture is more preferable than the culture with shaking. A principle of hemolytic activity assay is to utilize the fact that when erythrocyte membranes are destroyed, hemoglobins are released into the external erythrocytes to exhibit red color in the reaction medium, and the resulting red color is determined macroscopically. Erythrocytes used in the hemolytic reaction are not limited within human origins, and erythrocytes of any species, for example rabbit, horse, sheep, etc., can be used.

BEST MODE FOR CARRYING OUT THE INVENTION

Following examples are for the purpose of understanding the present invention completely and are not construed to limit the present invention.

Properties of strains and media used in examples of the present invention are shown in the following referential examples.

Referential Example 1

Enteropathogenic *Escherichia coli* (EPEC) E2348/69 (wild strain): (Cell, 91, 511–520, 1997; ATCC 12740); obtainable from American Type Culture Collection, 1080 University Boulevard, Manassas, Va., 20110–2209, USA

Referential Example 1-1

Figures 1, 2, 3:
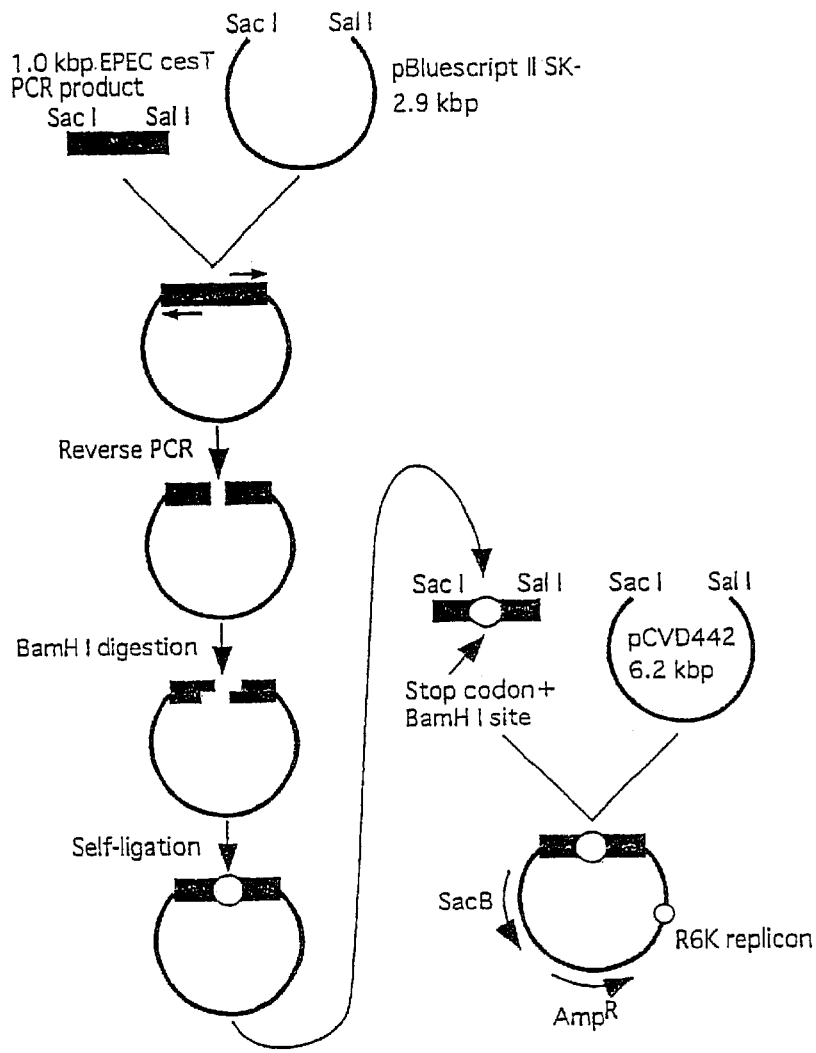
FIG. 1: A construction of recombinant plasmid used for preparation of EPEC cesT defective strain.
FIG. 2: A primer set (SEQ ID NOS 1–2) for amplifying gene used for construction of the recombinant plasmid of FIG. 1.
FIG. 3: A primer set (SEQ ID NOS 3–4) for inserting a termination codon and BamHI site by the reverse PCR used for construction of the recombinant plasmid of FIG. 1.

EPEC cesT defective strain: Tir specific chaperone defective strain (Molecular Microb. 33, 1162–1175, 1999); obtainable from Dr. Abe, Akio, The Kitasato Institute, 9-1, Shirokane 5-chome, Minato-ku, Tokyo, Japan Preparation of defective strain was performed by previously established procedure (Molecular Micro. 33, 1162–1175, 1999. FIG. 1 shows outlines of plasmid construction used for preparation of EPEC cesTdeficient strain. FIG. 2 shows a primer set for amplification of the gene used for the recombinant plasmid construction. FIG. 3 shows a primer set for inserting a terminal codon and BamHI site by reverse PCR which is used for the recombinant plasmid construction.

Preparation of a Recombinant Plasmid Used for Obtaining EPEC cesT defective Strain EPEC E2348/69 chromosomal DNA 0.5 µg was added to a solution 100 µl of 25 mM TAPS buffer (pH 9.3, 25° C.), 50 mM KCl, 2 mM $MgCl_2$, 1 mM 2-mercaptoethanol, 0.2 mM dNTP, 0.5 µM primer set (refer to FIG. 2) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, incubation at 72° C. for 5 minutes was performed. A cEsT genomic fragment 1.0 kbp amplified by PCR was collected by ethanol precipitation. The fragment was added to a solution 50 µl of 50 mM NaCl, 10 mM Tris-HCl (pH 7.9, 25° C.), 10 mM $MgCl_2$ and 1 mM dithiothreitol. A restriction enzyme SacI 5 units was added thereto and incubated at 37° C. for 2 hours.

After the incubation, 5M NaCl 1 µl and a restriction enzyme SalI 5 units were added and further incubated at 37° C. for 2 hours. After treatment with the restriction enzymes, DNA fragments were purified by agarose electrophoresis. The purified DNA fragments 0.1 µg and the restriction enzyme SalI splitted pBluescript IISK–(Stratagene Inc. USA) 0.2 µg were added to a solution 20 µl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. E. coli was transformed by this ligase solution to obtain a recombinant plasmid which was integrated with the genomic fragment.

Termination codon was inserted into the central region of cesT gene in the obtained recombinant plasmid by reverse PCR (Molecular Microb. 33, 1162–1175, 1999). The recombinant plasmid 0.05 µg was added to a solution 100 µl of 25 mM TAPS buffer (pH 9.3, 25° C.), 50 mM KCl, 2 mM $MgCl_2$, 1 mM 2-mercaptoethanol, 0.2 mM dNTP, 0.5 µM primer set (refer to FIG. 3) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, incubation at 72° C. for 5 minutes was performed. The amplified genomic fragments by PCR were collected by treatment of ethanol precipitation.

The precipitate was added to a solution 50 µl of 50 mM NaCl, 10 mM Tris-HCl (pH 7.9, 25° C.), 10 mM $MgCl_2$ and 1 mM dithiothreitol. A restriction enzyme BamHI 5 units was added thereto, incubated at 37° C. for 2 hours and purified by agarose electrophoresis. The purified DNA fragments were added to a solution 20 µl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. E. coli was transformed by this ligase solution to obtain a recombinant plasmid which was integrated with the termination codon in the translated region of the genomic fragment.

One µg of the recombinant plasmid integrated with the genomic fragment containing the termination codon was added to a solution 50 µl of 50 mM NaCl, 10 mM Tris-HCl (pH 7.9, 25° C.), 10 mM $MgCl_2$ and 1 mM dithiothreitol. A restriction enzyme SacI 5 units was added thereto and incubated at 37° C. for 2 hours.

After the incubation, 5M NaCl 1 µl and a restriction enzyme SalI 5 units were added and further incubated at 37° C. for 2 hours. After treatment with the restriction enzymes, DNA fragments were purified by agarose electrophoresis. The purified DNA fragments 0.1 µg and pCVD442 (Infect. Immun. 59, 4310–4317, 1991) 0.2 µg splitted by the restriction enzymes SalI and SacI were added to a solution 20 µl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. E. coli Sm10λpir (Bio. Technology, 1, 784–791, 1983) was transformed by this ligase solution to obtain a recombinant plasmid which was integrated with the genomic fragment.

Preparation of EPEC cesT Lacking Strain

EPEC E2348/69 was inoculated in LB medium 20 ml and shake cultured at 37° C. for overnight. Bacterial cells were collected by centrifugation from the cultured medium, suspended in LB medium 1 ml, and each 0.1 ml of the suspension was inoculated in LB agar medium containing nalidixic acid (30 µg/ml) and cultured at 37° C. for overnight. The obtained colonies were streaked on the LB agar medium containing nalidixic acid (30 µg/ml) and established the nalidixic acid resistant strain. Using the nalidixic acid resistant strain, a defective strain was prepared. Preparation of the defective strain was performed by previously established technique (Molecular Microb. 33, 1162–1175, 1999). Namely, E. coli Sm10λpir was transformed by using recombinant plasmid containing genomic fragment, to which a termination codon was inserted, and the transformant was streaked on the LB agar medium using cotton bud. Nalidixic acid resistant EPEC E2348/69 was further streaked on the streaked bacterial cells. The LB agar medium streaked with two bacterial cells was cultured at 37° C. for 6 hours.

The mixture of these two bacterial cells was streaked on the LB medium containing nalidixic acid (30 µg/ml) and ampicillin (50 µg/ml) and cultured at 37° C. for overnight to select bacterial cells integrated with the recombinant plasmid, by which mutation is generated. The appeared bacterial colonies were streaked on the LB agar medium containing nalidixic acid (30 µg/ml) and ampicillin (50 µg/ml) and were confirmed as resistant to both nalidixic acid and ampicillin. The confirmed bacterial colonies were inoculated in LB liquid medium containing nalidixic acid (30 µg/ml) and shake cultured at 37° C. for 3.5 hours. The bacterial cells were streaked on the sucrose agar medium containing nalidixic acid (30 µg/ml). Chromosomal DNA was prepared from the obtained colonies and EPEC cesT defective strain was confirmed.

Confirmation of EPEC cesT Defective Strain

The chromosomal DNA was prepared from the defective strain and the prepared chromosomal DNA 0.5 µg was added to a solution 100 µl of 25 mM TAPS buffer (pH 9.3, 25° C.), 50 mM KCl, 2 mM $MgCl_2$, 1 mM 2-mercaptoethanol, 0.2 mM dNTP, 0.5 µM primer set (refer to FIG. 2) and 2.5 units Takara EX Taq (Takara Shuzo, Japan). The mixture was treated for PCR using Mastercycler gradient (Eppendorf Inc.

Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, further incubation at 72° C. for 5 minutes was performed. The genomic fragments amplified by PCR were collected by ethanol precipitation, and the fragments were added to a solution 50 µl of 50 mM NaCl, 10 mM Tris-HCl (pH 7.9, 25° C.), 10 mM $MgCl_2$ and 1 mM dithiothreitol. A restriction enzyme BamHI 5 units was added thereto, incubated at 37° C. for 2 hours, and treated by agarose electrophoresis. The defective strain was determined by that the PCR amplified DNA fragment was digested by the restriction enzyme BamHI, which was inserted into immediately downstream of the termination codon, and the fragments were splitted into two fragments or not.

Referential Example 1-2
EPEC sepB Defective Strain

Figures 4, 5, 6:
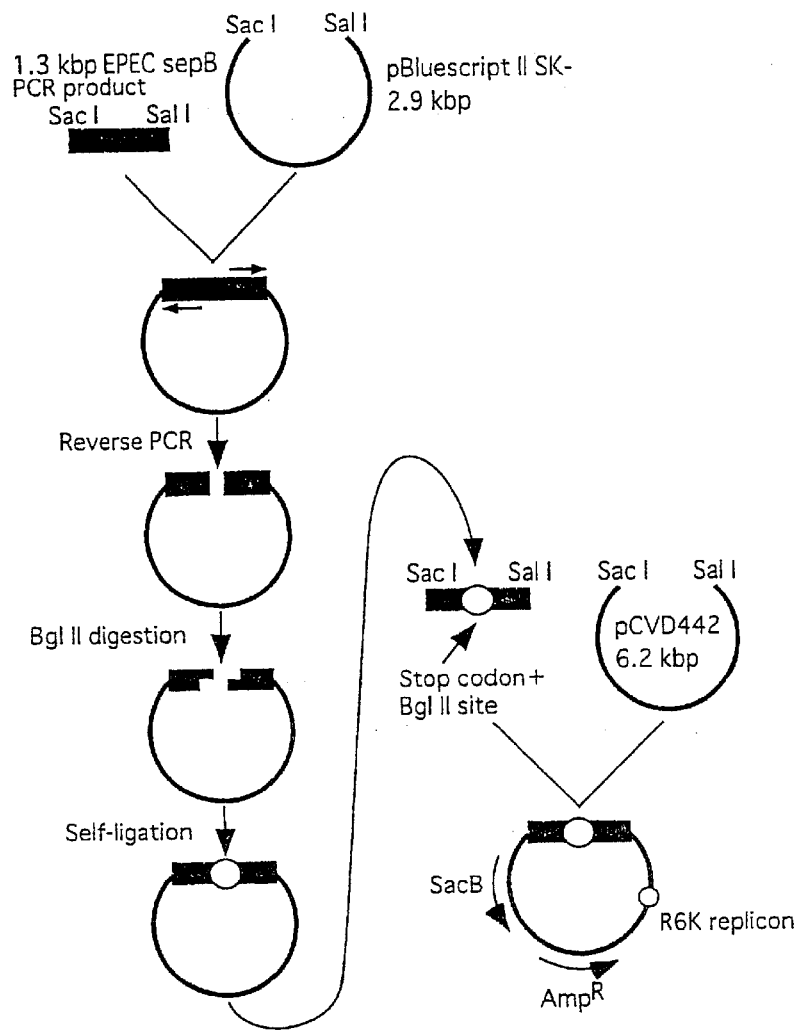
FIG. 4: A construction of a recombinant plasmit used for preparation of EPEC sepB defective strain.
FIG. 5: A primer set (SEQ ID NOS 5–6) for amplifying gene used for construction of the recombinant plasmid of FIG. 4.
FIG. 6: A primer set (SEQ ID NOS 7–8) for inserting a termination codon and BglII site by the reverse PCR used for construction of the recombinant plasmid of FIG. 4.

EPEC sepB defective strain: a strain lacking type III secretory mechanism (Proc. Natl. Acad. Sci., USA 92, 7996–8000, 1995; obtainable from Center for Vaccine Development and Department of Microbiology and Immunology, University of Maryland School of Medicine, U.S.A., Dr. James B. Kaper).
Preparation of Recombinant Plasmid Used for Obtaining EPEC sepB Defective Strain FIG. 4 shows a construction of a recombinant plasmid used for preparation of EPEC sepB defective strain. FIG. 5 shows a primer set for amplifying gene used for the construction of the recombinant plasmid. FIG. 6 shows a primer set for inserting a termination codon and a BglII site by the reverse PCR used for construction of the recombinant plasmid.

EPEC E2348/69 chromosomal DNA 0.5 µg was added to a solution 100 µl of 25 mM TAPS buffer (pH 9.3, 25° C.), 50 mM KCl, 2 mM $MgCl_2$, 1 mM 2-mercaptoethanol, 0.2 mM dNTP, 0.5 µM primer set (refer to FIG. 5) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, incubation at 72° C. for 5 minutes was performed. A sepB genomic fragment 1.0 kbp amplified by PCR was collected by ethanol precipitation. The fragment was added to a solution 50 µl of 50 mM NaCl, 10 mM Tris-HCl (pH 7.9, 25° C.), 10 mM $MgCl_2$ and 1 mM dithiothreitol. A restriction enzyme SacI 5 units was added thereto and incubated at 37° C. for 2 hours.

After the incubation, 5M NaCl 1 µl and a restriction enzyme SalI 5 units were added and further incubated at 37° C. for 2 hours. After treatment with the restriction enzymes, DNA fragments were purified by agarose electrophoresis. The purified DNA fragments 0.1 µg and pBluescript IISK (Stratagene Inc. USA) 0.2 µg splitted by restriction enzymes SalI and SacI were added to a solution 20 µl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. E. coli was transformed by this ligase solution to obtain a recombinant plasmid which was integrated with the genomic fragment.

Termination codon was inserted into the central region of sepB gene in the obtained recombinant plasmid by reverse PCR. The recombinant plasmid 0.05 µg was added to a solution 100 µl of 25 mM TAPS buffer (pH 9.3, 25° C.), 50 mM KCl, 2 mM $MgCl_2$, 1 mM 2-mercaptoethanol, 0.2 mM dNTP, 0.5 µM primer set (refer to FIG. 6) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, incubation at 72° C. for 5 minutes was performed. The amplified genomic fragments by PCR were collected by treatment of ethanol precipitation.

The precipitate was added to a solution 50 µl of 100 mM NaCl, 10 mM Tris-HCl (pH 7.9, 25° C.), 10 mM $MgCl_2$ and 1 mM dithiothreitol. A restriction enzyme BglII 5 units was added thereto, incubated at 37° C. for 2 hours and purified by agarose electrophoresis. The purified DNA fragments were added to a solution 20 µl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. E. coli was transformed by this ligase solution to obtain a recombinant plasmid which was integrated with the termination codon in the translated region of the genomic fragment.

One µg of the recombinant plasmid integrated with the genomic fragment containing the termination codon was added to a solution 50 µl of 50 mM NaCl, 10 mM Tris-HCl (pH 7.9, 25° C.), 10 mM $MgCl_2$ and 1 mM dithiothreitol. A restriction enzyme SacI 5 units was added thereto and incubated at 37° C. for 2 hours. After the incubation, 5M NaCl 1 µl and a restriction enzyme SalI 5 units were added and further incubated at 37° C. for 2 hours. After treatment with the restriction enzymes, DNA fragments were purified by agarose electrophoresis. The purified DNA fragments 0.1 µg and pCVD442 (Infect. Immun. 59, 4310–4317, 1991) 0.2 µg splitted by the restriction enzymes SalI and SacI were added to a solution 20 µl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. E. coli Sm10λpir (Bio. Technology, 1, 784–791, 1983) was transformed by this ligase solution to obtain a recombinant plasmid which was integrated with the genomic fragment.
Preparation of EPEC sepB Lacking Strain The preparation of the defective strain was performed by using the same procedure as in referential example 1-1. EPEC E2348/69 was inoculated in LB medium 20 ml and shake cultured at 37° C. for overnight. Bacterial cells were collected by centrifugation of the cultured medium, suspended in LB medium 1 ml, and each 0.1 ml of the suspension was inoculated in LB agar medium containing nalidixic acid (30 µg/ml) and cultured at 37° C. for overnight. The obtained colonies were streaked on the LB agar medium containing nalidixic acid (30 µg/ml) and established the nalidixic acid resistant strain. Using the nalidixic acid resistant strain, a defective strain was prepared. Preparation of the defective strain was performed by previously established technique (Molecular Microb. 33, 1162–1175, 1999). Namely, E. coli Sm10λpir was transformed by using recombinant plasmid containing genomic fragment, to which a termination codon was inserted, and the transformant was streaked on the LB agar medium using cotton bud. Nalidixic acid resistant EPEC E2348/69 was further streaked on the streaked bacterial cells. The LB agar medium streaked with two bacterial cells was cultured at 37° C. for 6 hours.

The mixture of these two bacterial cells was streaked on the LB medium containing nalidixic acid (30 µg/ml) and ampicillin (50 µg/ml) and standing cultured at 37° C. for overnight to select bacterial cells integrated with the recombinant plasmid, by which mutation is generated. The appeared bacterial colonies were streaked on the LB agar medium containing nalidixic acid (30 μg/ml) and ampicillin (50 μg/ml) and were confirmed as resistant to both nalidixic acid and ampicillin. The confirmed bacterial colonies were inoculated in LB liquid medium containing nalidixic acid (30 μg/ml) and shake cultured at 37° C. for 3.5 hours. The bacterial cells were streaked on the sucrose agar medium containing nalidixic acid (30 μg/ml). Chromosomal DNA was prepared from the obtained colonies and EPEC sepB defective strain was prepared.

Confirmation of EPEC sepB Defective Strain

The chromosomal DNA was prepared from the defective strain and the prepared chromosomal DNA 0.5 μg was added to a solution 100 μl of 25 mM TAPS buffer (pH 9.3, 25° C.), 50 mM KCl, 2 mM $MgCl_2$, 1 mM 2-mercaptoethanol, 0.2 mM dNTP, 0.5 μM primer set (refer to FIG. 5) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, further incubation at 72° C. for 5 minutes was performed. The genomic fragments amplified by PCR were collected by ethanol precipitation, and the fragments were added to a solution 50 μl of 50 mM NaCl, 10 mM Tris-HCl (pH 7.9, 25° C.), 10 mM $MgCl_2$ and 1 mM dithiothreitol. A restriction enzyme BglII 5 units was added thereto, incubated at 37° C. for 2 hours, and treated by agarose electrophoresis. The defective strain was determined by that the PCR amplified DNA fragment was digested by the restriction enzyme BglII, which was inserted into immediately downstream of the termination codon, and the fragments were splitted into two fragments or not.

Referential Example 1-3

EPEC espa Defective Strain

EPEC espa defective strain: a strain lacking type III secretory protein espA (Molecular Microb., 20, 313–323, 1996; obtainable from Biotechnology Laboratory, University of British Columbia, Canada, Dr. B. Brett Finlay or Dr. Abe, Akio, The Kitasato Institute, Sirokane 5-9-1, Minato-ku, Tokyo, Japan.

Figures 7, 8, 9:
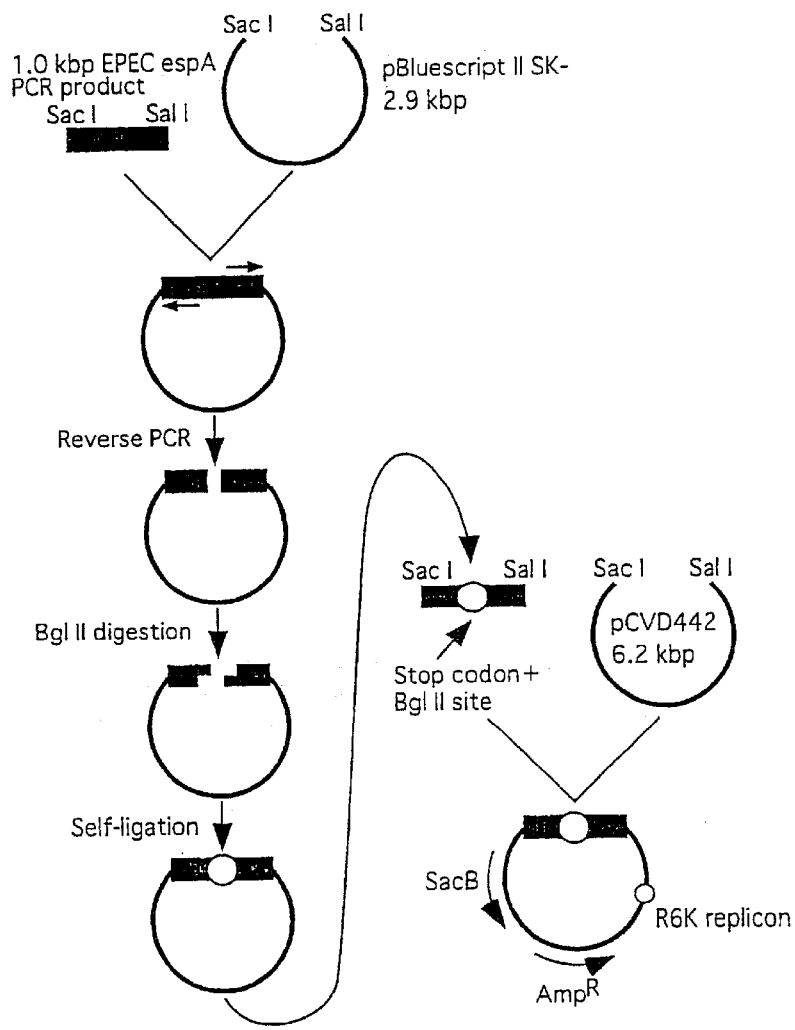
FIG. 7: A construction of a recombinant plasmid used for preparation of EPEC espA defective strain.
FIG. 8: A primer set (SEQ ID NOS 9–10) for amplifying gene used for construction of the recombinant plasmid of FIG. 7.
FIG. 9: A primer set (SEQ ID NOS 11–12) for inserting a termination codon and BglII site by the reverse PCR used for construction of the recombinant plasmid of FIG. 7.

Preparation of Recombinant Plasmid Used for Obtaining EPEC espA Defective Strain FIG. 7 shows a construction of a plasmid used for preparation of EPEC espa defective strain. FIG. 8 shows a primer set for amplifying gene used for the construction of the recombinant plasmid. FIG. 9 shows a primer set for inserting a termination codon and a BglII site by the reverse PCR used for construction of the recombinant plasmid.

EPEC E2348/69 chromosomal DNA 0.5 μg was added to a solution 100 μl of 25 mM TAPS buffer (pH 9.3, 25° C.), 50 mM KCl, 2 mM $MgCl_2$, 1 mM 2-mercaptoethanol, 0.2 mM dNTP, 0.5 μM primer set (refer to FIG. 8) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, incubation at 72° C. for 5 minutes was performed. The espA genomic fragment 1.0 kbp amplified by PCR was collected by ethanol precipitation. The fragment was added to a solution 50 μl of 50 mM NaCl, 10 mM Tris-HCl (pH 7.9, 25° C.), 10 mM $MgCl_2$ and 1 mM dithiothreitol. A restriction enzyme SacI 5 units was added thereto and incubated at 37° C. for 2 hours.

After the incubation, 5M NaCl 1 μl and a restriction enzyme SalI 5 units were added and further incubated at 37° C. for 2 hours. After treatment with the restriction enzymes, DNA fragments were purified by agarose electrophoresis. The purified DNA fragments 0.1 μg and pBluescript IISK⁻ (Stratagene Inc. USA) 0.2 μg splitted by restriction enzymes SalI and SacI were added to a solution 20 μl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. E. coli was transformed by this ligase solution to obtain a recombinant plasmid which was integrated with each genomic fragment.

Termination codon was inserted into the central region of espA gene in the obtained recombinant plasmid by reverse PCR. The recombinant plasmid 0.05 μg was added to a solution 100 μl of 25 mM TAPS buffer (pH 9.3, 25° C.), 50 mM KCl, 2 mM $MgCl_2$, 1 mM 2-mercaptoethanol, 0.2 mM dNTP, 0.5 μM primer set (refer to FIG. 9) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 5 minutes were repeated for 30 cycles. After 30 cycles of amplification, incubation at 72° C. for 5 minutes was performed. The amplified genomic fragments by PCR were collected by treatment of ethanol precipitation.

The precipitate was added to a solution 50 μl of 100 mM NaCl, 10 mM Tris-HCl (pH 7.9, 25° C.), 10 mM $MgCl_2$ and 1 mM dithiothreitol. A restriction enzyme BglII 5 units was added thereto, incubated at 37° C. for 2 hours and purified by agarose electrophoresis. The purified DNA fragments were added to a solution 20 μl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. E. coli was transformed by this ligase solution to obtain a recombinant plasmid which was integrated with the termination codon in the translated region of the genomic fragment.

One μg of the recombinant plasmid integrated with the genomic fragment containing the termination codon was added to a solution 50 μl of 50 mM NaCl, 10 mM Tris-HCl (pH 7.9, 25° C.), 10 mM $MgCl_2$ and 1 mM dithiothreitol. A restriction enzyme SacI 5 units was added thereto and incubated at 37° C. for 2 hours. After the incubation, 5M NaCl 1 μl and a restriction enzyme SalI 5 units were added and further incubated at 37° C. for 2 hours. After treatment with the restriction enzymes, DNA fragments were purified by agarose electrophoresis. The purified DNA fragments 0.1 μg and pCVD442 (Infect. Immun. 59, 4310–4317, 1991) 0.2 μg splitted by the restriction enzymes SalI and SacI were added to a solution 20 μl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. E. coli Sm10λpir (Bio. Technology, 1, 784–791, 1983) was transformed by this ligase solution to obtain a recombinant plasmid which was integrated with the genomic fragment.

Preparation of EPEC espA Lacking Strain

The preparation of the defective strain was performed by using the same procedure as in referential example 1-1. The bacteria was inoculated in LB medium 20 ml and shake cultured at 37° C. for overnight. Bacterial cells were collected by centrifugation of the cultured medium, suspended in LB medium 1 ml, and each 0.1 ml of the suspension was inoculated in LB agar medium containing nalidixic acid (30 μg/ml) and cultured at 37° C. for overnight. The obtained colonies were streaked on the LB agar medium containing nalidixic acid (30 μg/ml) to establish the nalidixic acid resistant strain. Using the nalidixic acid resistant strain, a defective strain was prepared. Preparation of the defective strain was performed by previously established technique (Molecular Microb. 33, 1162–1175, 1999). Namely, *E. coli* Sm10λpir was transformed by using recombinant plasmid containing genomic fragment, to which a termination codon was inserted, and the transformant was streaked on the LB agar medium using cotton bud. Nalidixic acid resistant EPEC E2348/69 was further streaked on the streaked bacterial cells. The LB agar medium streaked with two bacterial cells was cultured at 37° C. for 6 hours.

The mixture of these two bacterial cells was streaked on the LB medium containing nalidixic acid (30 μg/ml) and ampicillin (50 μg/ml) and standing cultured at 37° C. for overnight to select bacterial cells integrated with the recombinant plasmid, by which mutation is generated. The appeared bacterial colonies were streaked on the LB agar medium containing nalidixic acid (30 μg/ml) and ampicillin (50 μg/ml) and were confirmed as resistant to both nalidixic acid and ampicillin. The confirmed bacterial colonies were inoculated in LB liquid medium containing nalidixic acid (30 μg/ml) and shake cultured at 37° C. for 3.5 hours. The bacterial cells were streaked on the sucrose agar medium containing nalidixic acid (30 μg/ml). Chromosomal DNA was prepared from the obtained colonies and EPEC espA defective strain was prepared.

Confirmation of EPEC espA Defective Strain

The chromosomal DNA was prepared from the defective strain and the prepared chromosomal DNA 0.5 μg was added to a solution 100 μl of 25 mM TAPS buffer (pH 9.3, 25° C.), 50 mM KCl, 2 mM MgCl$_2$, 1 mM 2-mercaptoethanol, 0.2 mM dNTP, 0.5 μM primer set (refer to FIG. 8) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, further incubation at 72° C. for 5 minutes was performed. The genomic fragments amplified by PCR were collected by ethanol precipitation, and the fragments were added to a solution 50 μl of 100 mM NaCl, 10 mM Tris-HCl (pH 7.9, 25° C.), 10 mM MgCl$_2$ and 1 mM dithiothreitol. A restriction enzyme BglII 5 units was added thereto, incubated at 37° C. for 2 hours, and treated by agarose electrophoresis. The defective strain was determined by that the PCR amplified DNA fragment was digested by the restriction enzyme BglII, which was inserted into immediately downstream of the termination codon, and the fragments were splitted into two fragments or not.

Referential Example 1-4

EPEC espB Defective Strain

EPEC espB defective strain: a strain lacking type III secretory protein espB (J. Bacteriol., 175, 4670–4680, 1993; obtainable from Center for Vaccine Development and Department of Microbiology and Immunology, University of Maryland School of Medicine, U.S.A., Dr. James B. Kaper or Dr. Abe, Akio, The Kitasato Institute, Sirokane 5-9-1, Minato-ku, Tokyo, Japan.

Figures 10, 11, 12:
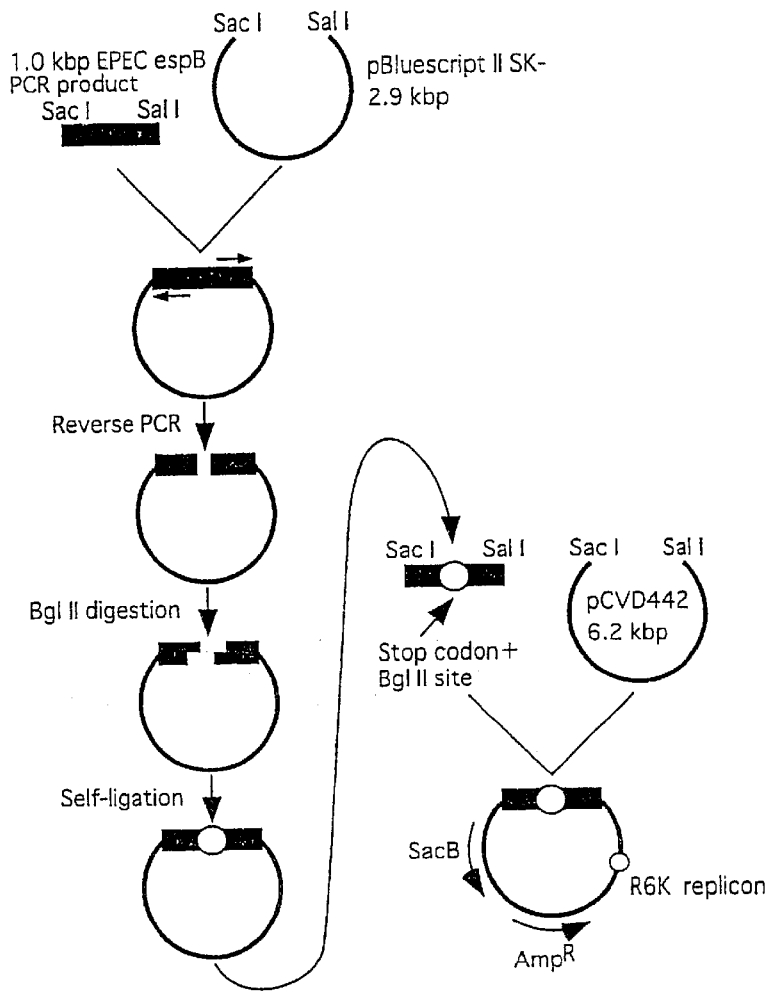
FIG. 10: A construction of a recombinant plasmid used for preparation of EPEC espB defective strain.
FIG. 11: A primer set (SEQ ID NOS 13–14) for amplifying gene used for construction of the recombinant plasmid of FIG. 10.
FIG. 12: A primer set (SEQ ID NOS 15–16) for inserting a termination codon and BglII site by the reverse PCR used for construction of the recombinant plasmid of FIG. 10.

Preparation of Recombinant Plasmid Used for Obtaining EPEC espB Defective Strain FIG. 10 shows a construction of a plasmid used for preparation of EPEC espB defective strain. FIG. 11 shows a primer set for amplifying gene used for the construction of the recombinant plasmid. FIG. 12 shows a primer set for inserting a termination codon and a BglII site by the reverse PCR used for construction of the recombinant plasmid.

EPEC E2348/69 chromosomal DNA 0.5 ug was added to a solution 100 μl of 25 mM TAPS buffer (pH 9.3, 25° C.), 50 mM KCl, 2 mM MgCl$_2$, 1 mM 2-mercaptoethanol, 0.2 nM dNTP, 0.5 μM primer set (refer to FIG. 11) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, incubation at 72° C. for 5 minutes was performed. The espB genomic fragment 1.0 kbp amplified by PCR was collected by ethanol precipitation. The fragment was added to a solution 50 μl of 50 mM NaCl, 10 mM Tris-HCl (pH 7.9, 25° C.), 10 mM MgCl$_2$ and 1 mM dithiothreitol. A restriction enzyme SacI 5 units was added thereto and incubated at 37° C. for 2 hours.

After the incubation, 5M NaCl 1 μl and a restriction enzyme SalI 5 units were added and further incubated at 37° C. for 2 hours. After treatment with the restriction enzymes, DNA fragments were purified by agarose electrophoresis. The purified DNA fragments 0.1 μg and pBluescript IISK⁻ (Stratagene Inc. USA) 0.2 μg splitted by restriction enzymes SalI and SacI were added to a solution 20 μl of 50 mM Tris HCl (pH 7.6), 10 mM MgCl$_2$, 1 mM ATP, 5 mM dithiothreitol, 5% (w/v) polyethyleneglycol 8000 and T4 DNA ligase 1 unit and incubated at 16° C. for 16 hours. *E. coli* was transformed by this ligase solution to obtain a recombinant plasmid which was integrated with each genomic fragment.

Termination codon was inserted into the central region of espB gene in the obtained recombinant plasmid by reverse PCR. The recombinant plasmid 0.05 μg was added to a solution 100 μl of 25 mM TAPS buffer (pH 9.3, 25° C.), 50 mM KCl, 2 mM MgCl$_2$, 1 mM 2-mercaptoethanol, 0.2 mM dNTP, 0.5 μM primer set (refer to FIG. 12) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 5 minutes were repeated for 30 cycles. After 30 cycles of amplification, incubation at 72° C. for 5 minutes was performed. The amplified genomic fragments by PCR were collected by treatment of ethanol precipitation.

The precipitate was added to a solution 50 μl of 100 mM NaCl, 10 mM Tis-HCl (pH 7.9, 25° C.), 10 mM MgCl$_2$ and 1 mM dithiothreitol. A restriction enzyme BglII 5 units was added thereto, incubated at 37° C. for 2 hours and purified by agarose electrophoresis. The purified DNA fragments were added to a solution 20 μl of 50 mM Tris HCl (pH 7.6), 10 mM MgCl$_2$, 1 mM ATP, 5 mM dithiothreitol, 5% (w/v) polyethyleneglycol 8000 and T4 DNA ligase 1 unit and incubated at 16° C. for 16 hours. *E. coli* was transformed by this ligase solution to obtain a recombinant plasmid which was integrated with the termination codon in the translated region of the genomic fragment.

One μg of the recombinant plasmid integrated with the genomic fragment containing the termination codon was added to a solution 50 μl of 50 mM NaCl, 10 mM Tris-HCl (pH 7.9, 25° C.), 10 mM MgCl$_2$ and 1 mM dithiothreitol. A restriction enzyme SacI 5 units was added thereto and incubated at 37° C. for 2 hours. After the incubation, 5M NaCl 1 μl and a restriction enzyme SalI 5 units were added and further incubated at 37° C. for 2 hours. After treatment with the restriction enzymes, DNA fragments were purified by agarose electrophoresis. The purified DNA fragments 0.1 μg and pCVD442 (Infect. Immun. 59, 4310–4317, 1991) 0.2

μg splitted by the restriction enzymes SalI and SacI were added to a solution 20 μl of 50 mM Tris HCl (pH 7.6), 10 mM MgCl$_2$, 1 mM ATP, 5 mM dithiothreitol, 5% (w/v) polyethyleneglycol 8000 and T4 DNA ligase 1 unit and incubated at 16° C. for 16 hours. *E. coli* Sm10λpir (Bio. Technology, 1, 784–791, 1983) was transformed by this ligase solution to obtain a recombinant plasmid which was integrated with the genomic fragment.

Preparation of EPEC espB Lacking Strain

The preparation of the defective strain was performed by using the same procedure as in referential example 1-1. EPEC E2348/69 was inoculated in LB medium 20 ml and shake cultured at 37° C. for overnight. The bacterial cells were collected by centrifugation of the cultured medium, suspended in LB medium 1 ml, and each 0.1 ml of the suspension was inoculated in LB agar medium containing nalidixic acid (30 μg/ml) and cultured at 37° C. for overnight. The obtained colonies were streaked on the LB agar medium containing nalidixic acid (30 μg/ml) to establish the nalidixic acid resistant strain. Using the nalidixic acid resistant strain, a defective strain was prepared. Preparation of the defective strain was performed by previously established technique (Molecular Microb. 33, 1162–1175, 1999). Namely, *E. coli* Sm10λpir was transformed by using recombinant plasmid containing genomic fragment, to which a termination codon was inserted, and the transformant was streaked on the LB agar medium using cotton bud. Nalidixic acid resistant EPEC E2348/69 was further streaked on the streaked bacterial cells. The LB agar medium streaked with two bacterial cells was cultured at 37° C. for 6 hours.

The mixture of these two bacterial cells was streaked on the LB medium containing nalidixic acid (30 μg/ml) and ampicillin (50 μg/ml) and standing cultured at 37° C. for overnight to select bacterial cells integrated with the recombinant plasmid, by which mutation is generated. The appeared bacterial colonies were streaked on the LB agar medium containing nalidixic acid (30 μg/ml) and ampicillin (50 μg/ml) and were confirmed as resistant to both nalidixic acid and ampicillin. The confirmed bacterial colonies were inoculated in LB liquid medium containing nalidixic acid (30 μg/ml) and shake cultured at 37° C. for 3.5 hours. The bacterial cells were streaked on the. sucrose agar medium containing nalidixic acid (30 μg/ml). Chromosomal DNA was prepared from the obtained colonies and EPEC espB defective strain was prepared.

Confirmation of EPEC espB Defective Strain

The chromosomal DNA was prepared from the defective strain and the prepared chromosomal DNA 0.5 μg was added to a solution 100 μl of 25 mM TAPS buffer (pH 9.3, 25° C.), 50 mM KCl, 2 mM MgCl$_2$, 1 mM 2-mercaptoethanol, 0.2 mM dNTP, 0.5 μM primer set (refer to FIG. 11) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, further incubation at 72° C. for 5 minutes was performed. The genomic fragments amplified by PCR were collected by ethanol precipitation, and the fragments were added to a solution 50 μl of 100 mM NaCl, 10 mM Tris-HCl (pH 7.9, 25° C.), 10 mM MgCl$_2$ and 1 mM dithiothreitol. A restriction enzyme BglII 5 units was added thereto, incubated at 37° C. for 2 hours, and treated by agarose electrophoresis. The defective strain was determined by that the PCR amplified DNA fragment was digested by the restriction enzyme BglII, which was inserted into immediately downstream of the termination codon, and the fragments were splitted into two fragments or not.

Referential Example 1-5
EPEC espD Defective Strain

EPEC espD defective strain: a strain lacking type III secretory protein espD (Infect. Immun., 65, 2211–2217, 1997; obtainable from Divisions of Gastroenterology, University of Maryland School of Medicine, U.S.A., Dr. Michael S. Donnenerg or Dr. Abe, Akio, The Kitasato Institute, Sirokane 5-9-1, Minato-ku, Tokyo, Japan.

Figures 13, 14, 15:
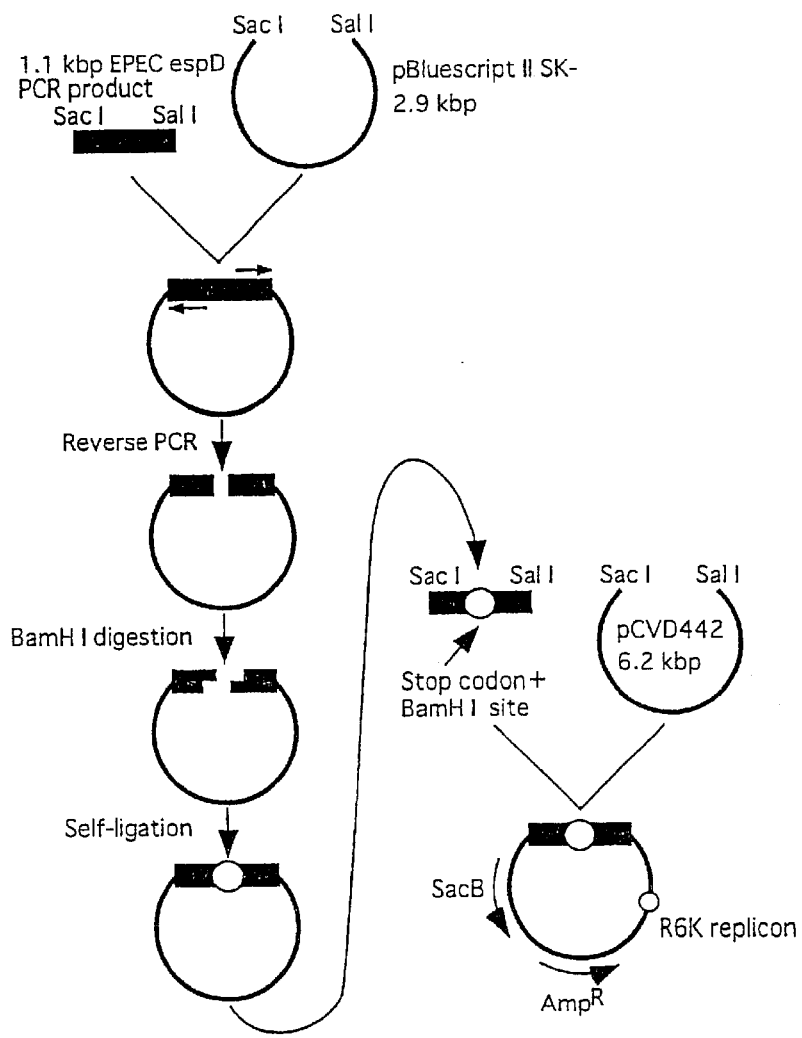
FIG. 13: A construction of a recombinant plasmid used for preparation of EPEC espD defective strain.
FIG. 14: A primer set (SEQ ID NOS 17–18) for amplifying gene used for construction of the recombinant plasmid of FIG. 13.
FIG. 15: A primer set (SEQ ID NOS 19–20) for inserting a termination codon and BamHI site by the reverse PCR used for construction of the recombinant plasmid of FIG. 13.

Preparation of Recombinant Plasmid Used for Obtaining EPEC espD Defective Strain FIG. 13 shows a construction of a plasmid used for preparation of EPEC espD defective strain. FIG. 14 shows a primer set for amplifying gene used for the construction of the recombinant plasmid. FIG. 15 shows a primer set for inserting a termination codon and a BamHI site by the reverse PCR used for construction of the recombinant plasmid.

EPEC E2348/69 chromosomal DNA 0.5 μg was added to a solution 100 μl of 25 mM TAPS buffer (pH 9.3, 25° C.), 50 mM KCl, 2 mM MgCl$_2$, 1 mM 2-mercaptoethanol, 0.2 mM dNTP, 0.5 μM primer set (refer to FIG. 14) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, incubation at 72° C. for 5 minutes was performed. The espD genomic fragment 1.1 kbp amplified by PCR was collected by ethanol precipitation. The fragment was added to a solution 50 μl of 50 mM NaCl, 10 mM Tris-HCl (pH 7.9, 25° C.), 10 mM MgCl$_2$ and 1 mM dithiothreitol. A restriction enzyme SacI 5 units was added thereto and incubatedat 37° C. for 2 hours.

After the incubation, 5M NaCl 1 μl and a restriction enzyme SalI 5 units were added and further incubated at 37° C. for 2 hours. After treatment with the restriction enzyme, DNA fragments were purified by agarose electrophoresis. The purified DNA fragments 0.1 μg and pBluescript IISK⁻ (Stratagene Inc. USA) 0.2 μg splitted by restriction enzymes SalI and SacI were added to a solution 20 μl of 50 mM Tris HCl (pH 7.6), 10 mM MgCl$_2$, 1 mM ATP, 5 mM dithiothreitol, 5% (w/v) polyethyleneglycol 8000 and T4 DNA ligase 1 unit and incubated at 16° C. for 16 hours. *E. coli* was transformed by this ligase solution to obtain a recombinant plasmid which was integrated with each genomic fragment.

Termination codon was inserted into the central region of espD gene in the obtained recombinant plasmid by reverse PCR. The recombinant plasmid 0.05 μg was added to a solution 100 μl of 25 mM TAPS buffer (pH 9.3, 25° C.), 50 mM KCl, 2 mM MgCl$_2$, 1 mM 2-mercaptoethanol, 0.2 mM dNTP, 0.5 μM primer set (refer to FIG. 15) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 5 minutes were repeated for 30 cycles. After 30 cycles of amplification, incubation at 72° C. for 5 minutes was performed. The amplified genomic fragments by PCR were collected by treatment of ethanol precipitation.

The precipitate was added to a solution 50 μl of 50 mM NaCl, 10 mM Tis-HCl (pH 7.9, 25° C.), 10 mM MgCl$_2$ and 1 mM dithiothreitol. A restriction enzyme BamHI 5 units was added thereto, incubated at 37° C. for 2 hours and purified by agarose electrophoresis. The purified DNA fragments were added to a solution 20 μl of 50 mM Tris HCl (pH 7.6), 10 mM MgCl$_2$, 1 mM ATP, 5 mM dithiothreitol, 5% (w/v) polyethyleneglycol 8000 and T4 DNA ligase 1 unit and incubated at 16° C. for 16 hours. *E. coli* was transformed by this ligase solution to obtain a recombinant plasmid which was integrated with the termination codon in the translated region of the genomic fragment.

One µg of the recombinant plasmid integrated with the genomic fragment containing the termination codon was added to a solution 50 µl of 50 mM NaCl, 10 mM Tris-HCl (pH 7.9, 25° C.), 10 mM MgCl$_2$ and 1 mM dithiothreitol. A restriction enzyme SacI 5 units was added thereto and incubated at 37° C. for 2 hours. After the incubation, 5M NaCl 1 µl and a restriction enzyme SalI 5 units were added and further incubated at 37° C. for 2 hours. After treatment with the restriction enzymes, DNA fragments were purified by agarose electrophoresis. The purified DNA fragments 0.1 µg and pCVD442 (Infect. Immun. 59, 4310–4317, 1991) 0.2 µg splitted by the restriction enzymes SalI and SacI were added to a solution 20 µl of 50 mM Tris HCl (pH 7.6), 10 mM MgCl$_2$, 1 mM ATP, 5 mM dithiothreitol, 5% (w/v) polyethyleneglycol 8000 and T4 DNA ligase 1 unit and incubated at 16° C. for 16 hours. *E. coli* Sm10λpir (Bio. Technology, 1, 784–791, 1983) was transformed by this ligase solution to obtain a recombinant plasmid which was integrated with each genomic fragment.

Preparation of EPEC espD Lacking Strain

The preparation of the defective strain was performed by using the same procedure as in referential example 1-1. EPEC E2348/69 was inoculated in LB medium 20 ml and shake cultured at 37° C. for overnight. The bacterial cells were collected by centrifugation of the cultured medium, suspended in LB medium 1 ml, and each 0.1 ml of the suspension was inoculated in LB agar medium containing nalidixic acid (30 µg/ml) and cultured at 37° C. for overnight. The obtained colonies were streaked on the LB agar medium containing nalidixic acid (30 µg/ml) to establish the nalidixic acid resistant strain. Using the nalidixic acid resistant strain, a defective strain was prepared. Preparation of the defective strain was performed by previously established technique (Molecular Microb. 33, 1162–1175, 1999). Namely, *E. coli* Sm10λpir was transformed by using recombinant plasmid containing genomic fragment, to which a termination codon was inserted, and the transformant was streaked on the LB agar medium using cotton bud. Nalidixic acid resistant EPEC E2348/69 was further streaked on the streaked bacterial cells. The LB agar medium streaked with two bacterial cells was cultured at 37° C. for 6 hours.

The mixture of these two bacterial cells was streaked on the LB medium containing nalidixic acid (30 µg/ml) and ampicillin (50 µg/ml) and standing cultured at 37° C. for overnight to select bacterial cells integrated with the recombinant plasmid, by which mutation is generated. The appeared bacterial colonies were streaked on the LB agar medium containing nalidixic acid (30 µg/ml) and ampicillin (50 µg/ml) and were confirmed as resistant to both nalidixic acid and ampicillin. The confirmed bacterial colonies were inoculated in LB liquid medium containing nalidixic acid (30 µg/ml) and shake cultured at 37° C. for 3.5 hours. The bacterial cells were streaked on the sucrose agar medium containing nalidixic acid (30 µg/ml). Chromosomal DNA was prepared from the obtained colonies and EPEC espD defective strain was prepared.

Confirmation of EPEC espD Defective Strain

The chromosomal DNA was prepared from the defective strain and the prepared chromosomal DNA 0.5 µg was added to a solution 100 µl of 25 mM TAPS buffer (H 9.3, 25° C.), 50 mM KCl, 2 mM MgCl$_2$, 1 mM 2-mercaptoethanol, 0.2 mM dNTP, 0.5 µM primer set (refer to FIG. 14) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, further incubation at 72° C. for 5 minutes was performed. The genomic fragments amplified by PCR were collected by ethanol precipitation, and the fragments were added to a solution 50 µl of 50 mM NaCl, 10 mM Tris-HCl (pH 7.9, 25° C.), 10 mM MgCl$_2$ and 1 mM dithiothreitol. A restriction enzyme BamHI 5 units was added thereto, incubated at 37° C. for 2 hours, and treated by agarose electrophoresis. The defective strain was determined by that the PCR amplified DNA fragment was digested by the restriction enzyme BamHI, which was inserted into immediately downstream of the termination codon, and the fragments were splitted into two fragments or not.

Referential Example 2

*Shigella flexneri* 2a YSH6000 (wild strain): Infect. Immun., 51, 470–475, 1986; ATCC 25875; obtainable from American Type Culture Collection, 10801 University Boulevard, Manassas, Va. 20110-2209, U.S.A.

Referential Example 2-1
*Shigella flexneri* ipaC Defective Strain

*Shigella flexneri* TK001: an ipaC lacking strain, a strain lacking type III secretory protein; obtainable from Dr. Chihiro Sasakawa, Institute of Medical Science, University of Tokyo, 4-6-1 Shirokanedai, Minato-ku, Tokyo, Japan.

Figures 16, 17, 18:
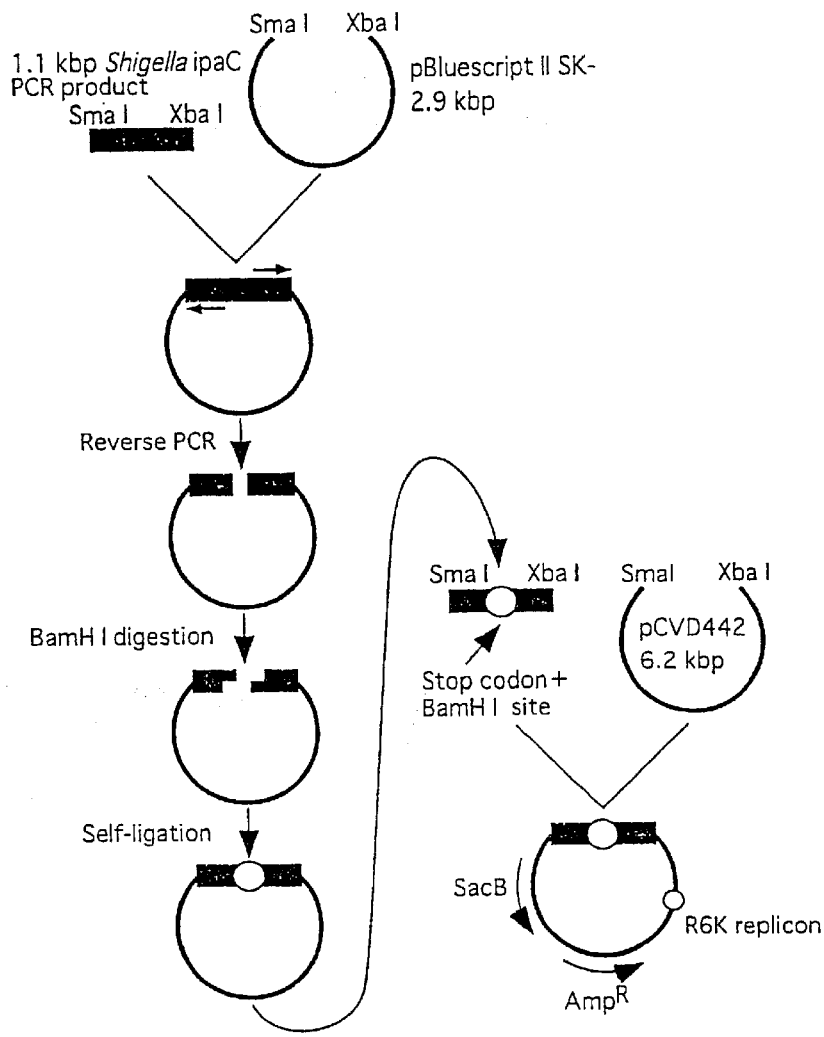
FIG. 16: A construction of a recombinant plasmid used for preparation of Shigella ipaC defective strain.
FIG. 17: A primer set (SEQ ID NOS 21–22) for amplifying gene used for construction of the recombinant plasmid of FIG. 16.
FIG. 18: A primer set (SEQ ID NOS 23–24) for inserting a termination codon and BamHI site by the reverse PCR used for construction of the recombinant plasmid of FIG. 16.

Preparation of Recombinant Plasmid Used for Obtaining Shigella ipaC Defective Strain FIG. 16 shows a construction of a plasmid used for preparation of ipaC defective strain. FIG. 17 shows a primer set for amplifying gene used for the construction of the recombinant plasmid. FIG. 18 shows a primer set for inserting a termination codon and a BamHI site by the reverse PCR used for construction of the recombinant plasmid.

*Shigella flexneri* 2a chromosomal DNA 0.5 µg was added to a solution 100 µl of 25 mM TAPS buffer (pH 9.3, 25° C.), 50 mM KCl, 2 mM MgCl$_2$, 1 mM 2-mercaptoethanol, 0.2 mM dNTP, 0.5 µM primer set (refer to FIG. 17) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72C for 2 minutes were repeated for 30 cycles. After 30 cycles of amplification, incubation at 72° C. for 5 minutes was performed. The ipaC genomic fragment 1.1 kbp amplified by PCR was collected by ethanol precipitation. The fragment was added to a solution 50 µl of 50 mM potassium acetate, 10 mM Tis-acetate (pH 7.9, 25° C.), 10 mM magnesium acetate and 1 mM dithiothreitol. Restriction enzymes SmaI and XbaI, 5 units respectively, were added thereto and incubated at 37° C. for 2 hours.

After treatment with the restriction enzyme, DNA fragments were purified by agarose electrophoresis. The purified DNA fragments 0.1 µg and pBluescript IISK⁻(Stratagene Inc. USA) 0.2 µg splitted by restriction enzymes SmaI and XbaI were added to a solution 20 µl of 50 mM Tris HCl (pH 7.6), 10 mM MgCl$_2$, 1 mM ATP, 5 mM dithiothreitol, 5% (w/v) polyethyleneglycol 8000 and T4 DNA ligase 1 unit and incubated at 16° C. for 16 hours. *E. coli* was transformed by this ligase solution to obtain a recombinant plasmid which was integrated with each genomic fragment.

Termination codon was inserted into the central region of ipaC gene in the obtained recombinant plasmid by reverse PCR. The recombinant plasmid 0.05 µg was added to a solution 100 µl of 25 mM TAPS buffer (pH 9.3, 25° C.), 50 mM KCl, 2 mM MgCl$_2$, 1 mM 2-mercaptoethanol, 0.2 mM dNTP, 0.5 µM primer set (refer to FIG. 18) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 5 minutes were repeated for 30 cycles. After 30 cycles of amplification, incubation at 72° C. for 5 minutes was performed. The amplified genomic fragments by PCR were collected by treatment of ethanol precipitation.

The precipitate was added to a solution 50 µl of 50 mM NaCl, 10 mM Tris-HCl (p 7.9, 25° C.), 10 mM MgCl$_2$ and 1 mM dithiothreitol. A restriction enzyme BamHI 5 units was added thereto, incubated at 37° C. for 2 hours and purified by agarose electrophoresis. The purified DNA fragments were added to a solution 20 µl of 50 mM Tris HCl (H 7.6), 10 mM MgCl$_2$, 1 mM ATP, 5 mM dithiothreitol, 5% (w/v) polyethyleneglycol 8000 and T4 DNA ligase 1 unit and incubated at 16° C. for 16 hours. E. coli was transformed by this ligase solution to obtain a recombinant plasmid which was integrated with the termination codon in the translated region of the genomic fragment.

One µg of the recombinant plasmid integrated with the genomic fragment containing the termination codon was added to a solution 50 µl of 50 mM potassium acetate, 10 mM Tris-acetate (pH 7.9, 25° C.), 10 mM magnesium acetate and 1 mM dithiothreitol. Restriction enzymes SmaI and XbaI, 5 units respectively, were added thereto and incubated at 37° C. for 2 hours. After treatment with the restriction enzymes, DNA fragments were purified by agarose electrophoresis. The purified DNA fragments 0.1 µg and pCVD442 (Infect. Immun. 59, 4310–4317, 1991) 0.2 µg splitted by the restriction enzymes SmaI and XbaI were added to a solution 20 µl of 50 mM Tris HCl (pH 7.6), 10 mM MgCl$_2$, 1 mM ATP, 5 mM dithiothreitol, 5% (w/v) polyethyleneglycol 8000 and T4 DNA ligase 1 unit and incubated at 16° C. for 16 hours. E. coli Sm10λpir (Bio. Technology, 1, 784–791, 1983) was transformed by this ligase solution to obtain a recombinant plasmid which was integrated with the genomic fragment.

Preparation of *Shigolla flexneri* ipaC Lacking Strain

The preparation of the defective strain was performed by using the same procedure as in referential example 1-1. *Shigella flexneri* 2a was inoculated in BHI medium (Difco Inc. U.S.A.) 20 ml and shake cultured at 37° C. for overnight. The bacterial cells were collected by centrifugation of the cultured medium, suspended in BHI medium 1 ml, and each 0.1 ml of the suspension was inoculated in LB agar medium containing nalidixic acid (30 µg/ml) and cultured at 37° C. for overnight. The obtained colonies were streaked on the LB agar medium containing nalidixic acid (30 µg/ml) to establish the nalidixic acid resistant strain. Using the nalidixic acid resistant strain, a defective strain was prepared. Preparation of the defective strain was performed by previously established technique (Molecular Microb. 33, 1162–1175, 1999). Namely, E. coli Sm10λpir was transformed by using recombinant plasmid containing genomic fragment, to which a termination codon was inserted, and the transformant was streaked on the LB agar medium using cotton bud. Nalidixic acid resistant *Shigella flexneri* 2a was further streaked on the streaked bacterial cells. The LB agar medium streaked with two bacterial cells was cultured at 37° C. for 6 hours.

The mixture of these two bacterial cells was streaked on the LB medium containing nalidixic acid (30 µg/ml) and ampicillin (50 µg/ml) and standing cultured at 37° C. for overnight to select bacterial cells integrated with the recombinant plasmid, by which mutation is generated. The appeared bacterial colonies were streaked on the LB agar medium containing nalidixic acid (30 µg/ml) and ampicillin (50 µg/ml) and were confirmed as resistant to both nalidixic acid and ampicillin. The confirmed bacterial colonies were inoculated in LB liquid medium containing nalidixic acid (30 µg/ml) and shake cultured at 37° C. for 3.5 hours. The bacterial cells were streaked on the sucrose agar medium containing nalidixic acid (30 µg/ml). Chromosomal DNA was prepared from the obtained colonies and *Shigella flexneri* ipaC defective strain was prepared.

Confirmation of *Shigella flexneri* ipaC Defective Strain

The chromosomal DNA was prepared from the defective strain and the prepared chromosomal DNA 0.5 µg was added to a solution 100 µl of 25 mM TAPS buffer (pH 9.3, 25° C.), 50 mM KCl, 2 mM MgCl$_2$, 1 mM 2-mercaptoethanol, 0.2 mM dNTP, 0.5 µM primer set (refer to FIG. 17) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, further incubation at 72° C. for 5 minutes was performed. The genomic fragments amplified by PCR were collected by ethanol precipitation, and the fragments were added to a solution 50 µl of 50 mM NaCl, 10 mM Tris-HCl (pH 7.9, 25° C.), 10 mM MgCl$_2$ and 1 mM dithiotlreitol. A restriction enzyme BamHI 5 units was added thereto, incubated at 37° C. for 2 hours, and treated by agarose electrophoresis. The defective strain was determined by that the PCR amplified DNA fragment was digested by the restriction enzyme BamHI, which was inserted into immediately downstream of the termination codon, and the fragments were splitted into two fragments or not.

Referential Example 3

*Salmonella typhimurium* SR11 (wild strain): J. Bacteriol., 174, 4338–4349, 1992; ATCC 14028; obtainable from American Type Culture Collection, 10801 University Boulevard, Manassas, Va. 20110-2209, U.S.A.

Referential Example 3-1

*Salmonella typhimurium* SB147 Defective Strain

*Salmonella typhimurium* SB147: an invA lacking strain, a strain lacking type III secretory mechanism (J. Bacteriol., 175, 4338–4349, 1992; obtainable from Boyer Center for Molecular Medicine, Yale School of Medicine, Dr. Jorge E. Galan).

Figures 19, 20, 21:
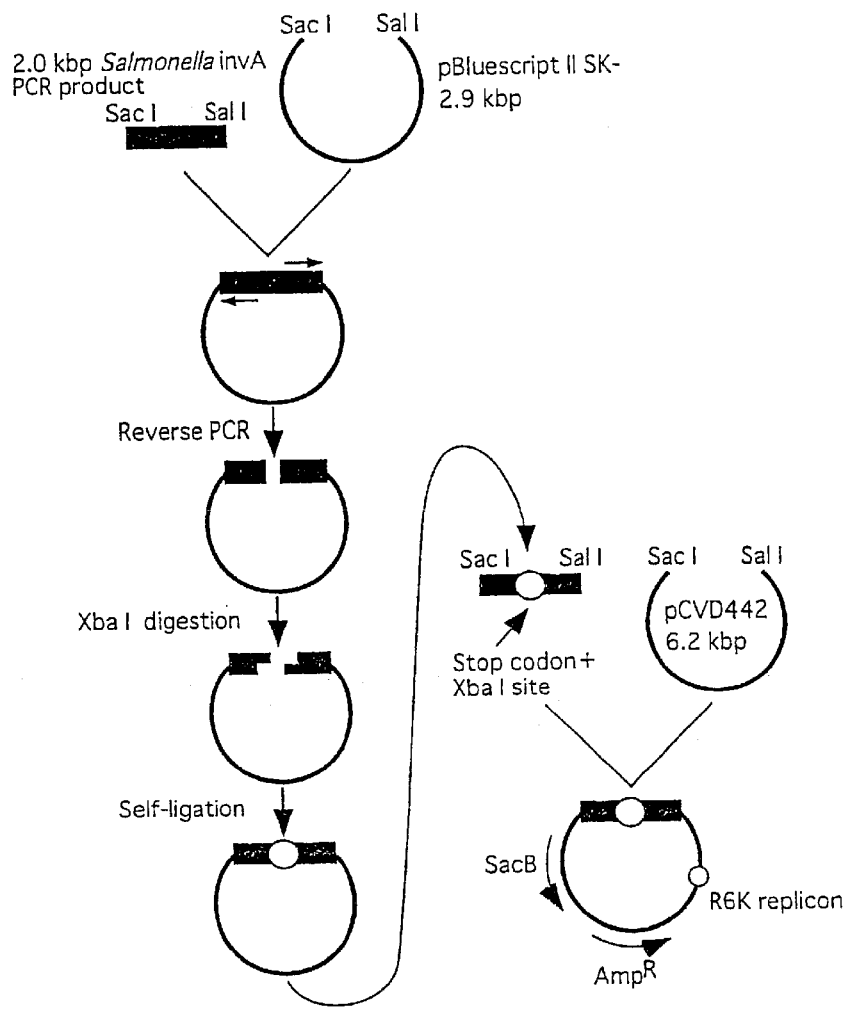
FIG. 19: A construction of a recombinant plasmid used for preparation of Salmonella invA defective strain.
FIG. 20: A primer set (SEQ ID NOS 25–26) for amplifying gene used for construction of the recombinant plasmid of FIG. 19.
FIG. 21: A primer set (SEQ ID NOS 27–28) for inserting a termination codon and XbaI site by the reverse PCR used for construction of the recombinant plasmid of FIG. 19.

Preparation of Recombinant Plasmid Used for Obtaining *Salmonella typhimurium* invA Defective Strain FIG. 19 shows a construction of a plasmid used for preparation of invA defective strain. FIG. 20 shows a primer set for amplifying gene used for the construction of the recombinant plasmid. FIG. 21 shows a primer set for inserting a termination codon and a XbaI site by the reverse PCR used for construction of the recombinant plasmid.

*Salmonella typhimurium* chromosomal DNA 0.5 µg was added to a solution 100 µl of 25 mM TAPS buffer (pH 9.3, 25° C.), 50 mM KCl, 2 mM MgCl$_2$, 1 mM 2-mercaptoethanol, 0.2 mM dNTP, 0.5 µM primer set (refer to FIG. 20) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, incubation at 72° C. for 5 minutes was performed. The invA genomic fragment 2.0 kbp amplified by PCR was collected by ethanol precipitation. The fragment was added to a solution 50 μl of 50 mM NaCl, 10 mM Tris-HCl (pH 7.9, 25° C.), 10 mM $MgCl_2$ and 1 mM dithiothreitol. Restriction enzyme SacI 5 units was added thereto and incubated at 37° C. for 2 hours.

After the reaction, 5 M NaCl and the restriction enzyme SalI 5 units were added and further incubated at 37° C. for 2 hours. After treatment with the restriction enzyme, DNA fragments were purified by agarose electrophoresis. The purified DNA fragments 0.1 μg and pBluescript IISK⁻ (Stratagene Inc. USA) 0.2 μg splitted by restriction enzymes SalI and SacI were added to a solution 20 μl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. *E. coli* was transformed by this ligase solution to obtain a recombinant plasmid which was integrated with the genomic fragment.

Termination codon was inserted into the central region of invA gene in the obtained recombinant plasmid by reverse PCR. The recombinant plasmid 0.05 μg was added to a solution 100 μl of 25 mM TAPS buffer (pH 9.3, 25° C.), 50 mM KCl, 2 mM $MgCl_2$, 1 mM 2-mercaptoethanol, 0.2 mM dNTP, 0.5 μM primer set (refer to FIG. 21) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 5 minutes were repeated for 30 cycles. After 30 cycles of amplification, incubation at 72° C. for 5 minutes was performed. The amplified genomic fragments by PCR were collected by treatment of ethanol precipitation.

The precipitate was added to a solution 50 μl of 50 mM NaCl, 10 mM Tris-HCl (pH 7.9, 25° C.), 10 mM $MgCl_2$ and 1 mM dithiothreitol. A restriction enzyme XbaI 5 units was added thereto, incubated at 37° C. for 2 hours and purified by agarose electrophoresis. The purified DNA fragments were added to a solution 20 μl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. *E. coli* was transformed by this ligase solution to obtain a recombinant plasmid which was integrated with the termination codon in the translated region of the genomic fragment.

One μg of the recombinant plasmid integrated with the genomic fragment containing the termination codon was added to a solution 50 μl of 50 mM NaCl, 10 mM Tris-HCl (pH 7.9, 25° C.), 10 mM $MgCl_2$ and 1 mM dithiothreitol. Restriction enzyme SacI 5 units was added thereto and incubated at 37° C. for 2 hours. After the incubation, 5 M NaCl 1μl and the restriction enzyme SalI 5 units were added and further incubated at 37° C. for 2 hours. After treatment with the restriction enzymes, DNA fragments were purified by agarose electrophoresis. The purified DNA fragments 0.1 μg and pCVD442 (Infect. Immun. 59, 4310–4317, 1991) 0.2 μg splitted by the restriction enzymes SalI and SacI were added to a solution 20 μl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. *E. coli* Sm10λpir (Bio. Technology, 1, 784–791, 1983) was transformed by this ligase solution to obtain a recombinant plasmid which was integrated with the genomic fragment.

Preparation of *Salmonella typhimurium* invA Lacking Strain

The preparation of the defective strain was performed by using the same procedure as in referential example 1-1. *Salmonella typhimurium* was inoculated in LB medium 20 ml and shake cultured at 37° C. for overnight. The bacterial cells were collected by centrifugation of the cultured medium, suspended in LB medium 1 ml, and each 0.1 ml of the suspension was inoculated in LB agar medium containing nalidixic acid (30 μg/ml) and cultured at 37° C. for overnight. The obtained colonies were streaked on the LB agar medium containing nalidixic acid (30 μg/ml) to establish the nalidixic acid resistant strain. Using the nalidixic acid resistant strain, a defective strain was prepared. Preparation of the defective strain was performed by previously established technique (Molecular Microb. 33, 1162–1175, 1999). Namely, *E. coli* Sm10λpir was transformed by using recombinant plasmid containing genomic fragment, to which a termination codon was inserted, and the transformant was streaked on the LB agar medium using cotton bud. Nalidixic acid resistant *Salmonella typhimurium* was further streaked on the streaked bacterial cells. The LB agar medium streaked with two bacterial cells was cultured at 37° C. for 6 hours.

The mixture of these two bacterial cells was streaked on the LB medium containing nalidixic acid (30 μg/ml) and ampicillin (50 μg/ml) and standing cultured at 37° C. for overnight to select bacterial cells integrated with the recombinant plasmid, by which mutation is generated. The appeared bacterial colonies were streaked on the LB agar medium containing nalidixic acid (30 μg/ml) and ampicillin (50 μg/ml) and were confirmed as resistant to both nalidixic acid and ampicillin. The confirmed bacterial colonies were inoculated in LB liquid medium containing nalidixic acid (30 μg/ml) and shake cultured at 37° C. for 3.5 hours. The bacterial cells were streaked on the sucrose agar medium containing nalidixic acid (30 μg/ml). Chromosomal DNA was prepared from the obtained colonies and *Salmonella typhimurium* invA defective strain was prepared.

Confirmation of *Salmonella typhimurium* invA Defective Strain

The chromosomal DNA was prepared from the defective strain and the prepared chromosomal DNA 0.5 μg was added to a solution 100 μl of 25 mM TAPS buffer (pH 9.3, 25° C.), 50 mM KCl, 2 mM $MgCl_2$, 1 mM 2-mercaptoethanol, 0.2 mM dNTP, 0.5 μM primer set (refer to FIG. 20) and 2.5 units Takara EX Taq (akara Shuzo, Japan). The mixture was treated for PCR using Mastercycler gradient (Eppendorf Inc. Germany). Conditions of PCR are: after heating at 94° C. for 6 minutes, incubations at 94° C. for 1 minute, at 58° C. for 1 minutes and at 72° C. for 2 minutes were repeated for 30 cycles. After 30 cycles of amplification, further incubation at 72° C. for 5 minutes was performed. The genomic fragments amplified by PCR were collected by ethanol precipitation, and the fragments were added to a solution 50 μl of 50 mM NaCl, 10 mM Tis-HCl (pH 7.9, 25° C.), 10 mM $MgCl_2$ and 1 mM dithiothreitol. A restriction enzyme XbaI 5 units was added thereto, incubated at 37° C. for 2 hours, and treated by agarose electrophoresis. The defective strain was determined by that the PCR amplified DNA fragment was digested by the restriction enzyme XbaI, which was inserted into immediately downstream of the termination codon, and the fragments were splitted into two fragments or not.

Referential Example 4
Psuedomonas

Pseudomonas aeruginosa PAO1: ATCC 15692; obtainable from American Type Culture Collection, 10801 University Boulevard, Manassas, Va. 20110-2209, U.S.A.

Referential Example 5
Genus Bordetella

Bordetella bronchiseptica S798 (wild strain): ATCC 780; obtainable from American Type Culture Collection, 10801 University Boulevard, Manassas, Va. 20110-2209, U.S.A.

Referential Example 5-1
Bordetella bronchiseptica S798 bscN Defective Strain Bordetella bronchiseptica S798 bscN defective strain; obtainable from Dr. Abe, Akio, The Kitasato Institute, Sirokane 5-9-1, Minato-ku, Tokyo, Japan.

Figures 22, 23, 24:
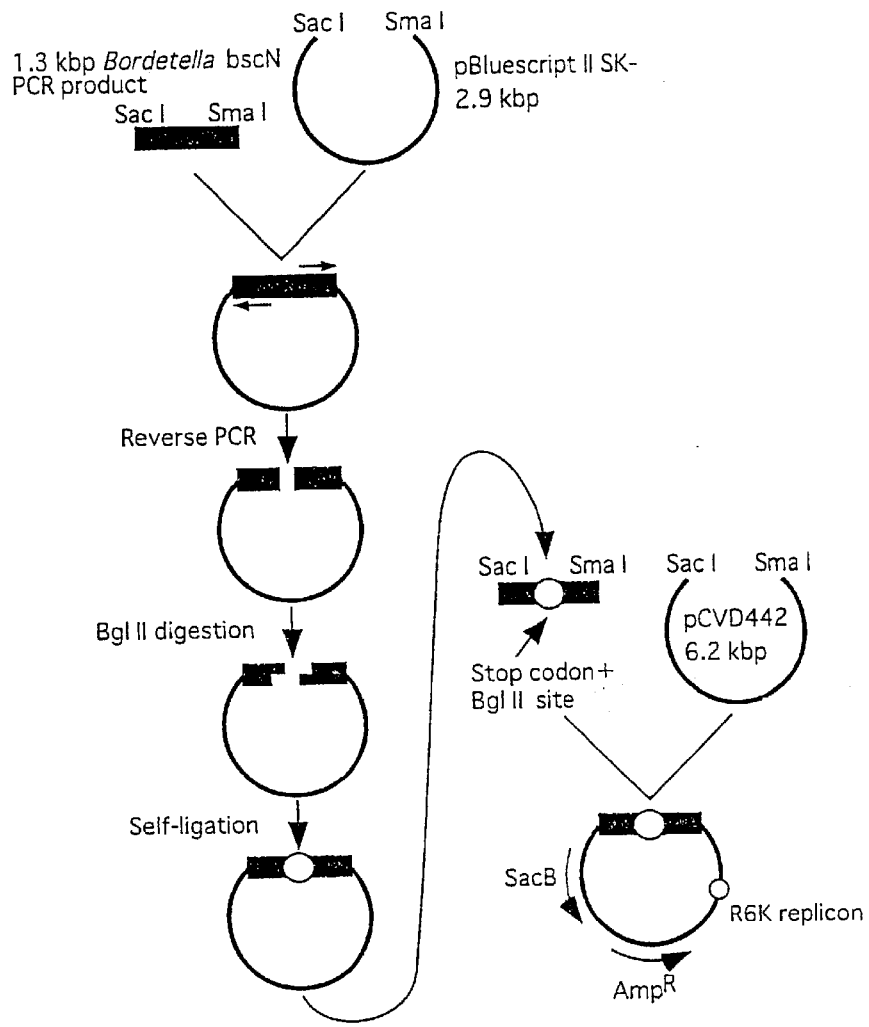
FIG. 22: A construction of a recombinant plasmid used for preparation of Bordetella bscN defective strain.
FIG. 23: A primer set (SEQ ID NOS 29–30) for amplifying gene used for construction of the recombinant plasmid of FIG. 22.
FIG. 24: A primer set (SEQ ID NOS 31–32) for inserting a termination codon and BglII site by the reverse PCR used for construction of the recombinant plasmid of FIG. 22.

Preparation of Recombinant Plasmid Used for Obtaining Bordetella bronchiseptica S798 bscN Defective Strain FIG. 22 shows a construction of a plasmid used for preparation of bscN defective strain. FIG. 23 shows a primer set for amplifying gene used for the construction of the recombinant plasmid. FIG. 24 shows a primer set for inserting a termination codon and a BglII site by the reverse PCR used for construction of the recombinant plasmid.

*Bordetella bronchiseptica* chromosomal DNA 0.5 μg was added to a solution 100 μl of 25 mM TAPS buffer (pH 9.3, 25° C.), 50 mM KCl, 2 mM $MgCl_2$, 1 mM 2-mercaptoethanol, 0.2 mM dNTP, 0.5 μM primer set (refer to FIG. 22) and 2.5 units Takara EX Taq (Takara Shuzo, Japan). The mixture was treated for PCR using Mastercycler gradient Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, incubation at 72° C. for 5 minutes was performed. The bscN genomic fragment 1.3 kbp amplified by PCR was collected by ethanol precipitation. The fragment was added to a solution 50 μl of 50 mM potassium acetate, 10 mM Tris-acetate (pH 7.9, 25° C.), 10 mM magnesium acetate and 1 mM dithiothreitol. Restriction enzymes SacI and SmaI, 5 units respectively, were added thereto and incubated at 37° C. for 2 hours.

After treatment with the restriction enzyme, DNA fragments were purified by agarose electrophoresis. The purified DNA fragments 0.1 μg and pbluescript IISK$^-$(Stratagene Inc. USA) 0.2 μg splitted by restriction enzymes SacI and SmaI were added to a solution 20 μl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. *E. coli* was transformed by this ligase solution to obtain a recombinant plasmid which was integrated with each genomic fragment.

Termination codon was inserted into the central region of the gene in the obtained recombinant plasmid by reverse PCR. The recombinant plasmid 0.05 μg was added to a solution 100 μl of 25 mM TAPS buffer (pH 9.3, 25° C.), 50 mM KCl, 2 mM $MgCl_2$, 1 mM 2-mercaptoethanol, 0.2 mM dNTP, 0.5 μM primer set (refer to FIG. 24) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 5 minute were repeated for 30 cycles. After 30 cycles of amplification, incubation at 72° C. for 5 minutes was performed. The amplified genomic fragments by PCR were collected by treatment of ethanol precipitation.

The precipitate was added to a solution 50 μl of 100 mM NaCl, 10 mM Tris-HCl (pH 7.9, 25° C.), 10 mM $MgCl_2$ and 1 mM dithiothreitol. A restriction enzyme BglII 5 units was added thereto, incubated at 37° C. for 2 hours and purified by agarose electrophoresis. The purified DNA fragments were added to a solution 20 μl of 50 mM Tis HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. *E. coli* was transformed by this ligase solution to obtain a recombinant plasmid which was integrated with the termination codon in the translated region of the genomic fragment.

One μg of the recombinant plasmid integrated with the genomic. fragment containing the termination codon was added to a solution 50 μl of 50 mM potassium acetate, 10 mM Tris-acetate (pH 7.9, 25° C.), 10 mM magnesium acetate and 1 mM dithiothreitol. Restriction enzymes SacI and SmaI, 5 units respectively, were added thereto and incubated at 37° C. for 2 hours. After treatment with the restriction enzymes, DNA fragments were purified by agarose electrophoresis. The purified DNA fragments 0.1 μg and pCVD442 (Infect. Immun. 59, 4310–4317, 1991) 0.2 μg splitted by the restriction enzymes SmaI and SacI were added to a solution 20 μl of 50 mM Tris HCl (pH 7.6), 10 mM $MgCl_2$, 1 mM ATP, 5 mM dithiothreitol, 5% (w/v) polyethyleneglycol 8000 and T4 DNA ligase 1 unit and incubated at 16° C. for 16 hours. *E. coli* Sm10λpir (Bio. Technology, 1, 784–791, 1983) was transformed by this ligase solution to obtain a recombinant plasmid which was integrated with the genomic fragment.

Preparation of *Bordetella bronchiseptica* S798 bscN Lacking Strain

The preparation of the defective strain was performed by using the same procedure as in referential example 1-1. *Bordetella bronchiseptica* was inoculated in LB medium 20 ml and shake cultured at 37° C. for overnight. The bacterial cells were collected by centrifugation of the cultured medium, suspended in LB medium 1 ml, and each 0.1 ml of the suspension was inoculated in LB agar medium containing nalidixic acid (30 μg/ml) and cultured at 37° C. for overnight. The obtained colonies were streaked on the LB agar medium containing nalidixic acid (30 μg/ml) to establish the nalidixic acid resistant strain. Using the nalidixic acid resistant strain, a defective strain was prepared. Preparation of the defective strain was performed by previously established technique (Molecular Microb. 33, 1162–1175, 1999). Namely, *E. coli* Sm10λpir was transformed by using recombinant plasmid containing genomic fragment, to which a termination codon was inserted, and the transformant was streaked on the LB agar medium using cotton bud. Nalidixic acid resistant *Bordetella bronchiseptica* was further streaked on the streaked bacterial cells. The LB agar medium streaked with two bacterial cells was cultured at 37° C. for 6 hours.

The mixture of these two bacterial cells was streaked on the LB medium containing nalidixic acid (30 μg/ml) and ampicillin (50 μg/ml) and standing cultured at 37° C. for overnight to select bacterial cells integrated with the recombinant plasmid, by which mutation is generated. The appeared bacterial colonies were streaked on the LB agar medium containing nalidixic acid (30 μg/ml) and ampicillin (50 μg/ml) and were confirmed as resistant to both nalidixic acid and ampicillin. The confirmed bacterial colonies were inoculated in LB liquid medium containing nalidixic acid (30 μg/ml) and shake cultured at 37° C. for 3.5 hours. The bacterial cells were streaked on the sucrose agar medium containing nalidixic acid (30 μg/ml). Chromosomal DNA was prepared from the obtained colonies and *Bordetella bronchiseptica* S798 bscN defective strain was prepared.

Confirmation of *Bordetella bronchiseptica* S798 bscN Defective Strain

The chromosomal DNA was prepared from the defective strain and the prepared chromosomal DNA 0.5 μg was added to a solution 100 μl of 25 mM TAPS buffer (pH 9.3, 25° C.), 50 mM KCl, 2 mM $MgCl_2$, 1 mM 2-mercaptoethanol, 0.2 mM dNTP, 0.5 μM primer set (refer to FIG. 23) and 2.5 units Takara EX Taq (Takara Shuzo, Japan). The mixture was treated for PCR using Mastercycler gradient (Eppendorf Inc. Germany). Conditions of PCR are: after heating at 94° C. for 5 minutes, incubations at 94° C. for 1 minute, at 58° C. for 1 minutes and at 72° C. for 2 minutes were repeated for 30 cycles. After 30 cycles of amplification, further incubation at 72° C. for 5 minutes was performed. The genomic fragments amplified by PCR were collected by ethanol precipitation, and the fragments were added to a solution 50 μl of 100 mM NaCl, 10 mM Tris-HCl (pH 7.9, 25° C.), 10 mM $MgCl_2$ and 1 mM dithiothreitol. A restriction enzyme BglII 5 units was added thereto, incubated at 37° C. for 2 hours, and treated by agarose electrophoresis. The defective strain was determined by that the PCR amplified DNA fragment was digested by the restriction enzyme BglII, which was inserted into immediately downstream of the termination codon, and the fragments were splitted into two fragments or not.

Referential Example 6

Sucrose Agar Medium

| | |
|---|---|
| Tryptone | 10.0 g |
| Yeast extract | 5.0 g |
| Sucrose | 50.0 g |
| Agar (Difco, U.S.A.) | 15.0 g |
| Distilled water | 1000 ml |

The above composition is autoclaved at 121° C. for 15 minutes.

Referential Example 7

M9 Medium

| | |
|---|---|
| Disodium hydrogenphosphate 7 hydrate | 12.8 g |
| Potassium dihydrogenphosphate | 3.0 g |
| Sodium chloride | 0.5 g |
| Ammonium chloride | 1.0 g |
| Distilled water | 1000 ml |

The above composition is autoclaved at 121° C. for 15 minutes, and the following composition is added aseptically.

| | |
|---|---|
| 20% glucose | 20.0 ml |
| 10% casamino acid | 10.0 ml |
| 1M magnesium sulfate | 1.0 ml |

Referential Example 8

LB Medium

| | |
|---|---|
| Tryptone | 10.0 g |
| Yeast extract | 5.0 g |
| Sodium chloride | 10.0 g |

The above is adjusted to pH 7.2 by adding sodium hydroxide and distilled water is added to total volume 1000 ml, and autoclaved at 121° C. for 15 minutes.

Referential Example 9

LB Agar Medium

| | |
|---|---|
| Tryptone | 10.0 g |
| Yeast extract | 5.0 g |
| Sodium chloride | 10.0 g |
| Agar (Difco, U.S.A.) | 15.0 g |
| Distilled water | 1000 ml |

The above is autoclaved at 121° C. for 15 minutes.

Referential Example 10

Stainer-Sholte Mdium

| | |
|---|---|
| Glutamic acid | 10.7 g |
| Proline | 0.24 g |
| Sodium chloride | 2.5 g |
| Potassium chloride | 0.2 g |
| Potassium dihydrogenphosphate | 0.5 g |
| Magnesium chloride 6 hydrate | 0.1 g |
| Calcium chloride | 0.02 g |
| Tris buffer | 6.1 g |
| Casamino acid | 10.0 g |
| Dimethyl β-cyclodextrin | 1.0 g |

The above composition is adjusted to pH 7.4 by adding hydrochloric acid and distilled water is added to total volume 1000 ml, and autoclaved at 121° C. for 15 minutes, then the following composition 10 ml is aseptically added to 1000 ml of the above.

| | |
|---|---|
| L-cysteine hydrochloride 1 hydrate | 4.0 g |
| Iron sulfate 7 hydrate | 1.0 g |
| Ascorbic acid | 40.0 g |
| Nicotinic acid | 0.4 g |
| Reduced form glutathione | 15.0 g |

Distilled water is added to total volume 1000 ml, and sterilized by filtration.

EXAMPLE 1-(1)

Culturing Method of Test Microorganisms

EPEC cesT lacking strain was inoculated in LB agar plate and cultured at 37° C. for overnight (about 16 hours). One bacterial colony was inoculated in to LB medium 3 ml and cultured at 37° C. for overnight without shaking. Bacterial culture 0.5 ml was inoculated to M9 medium 50 ml, and incubated at 37° C. for further 4 hours without shaking. Cultured liquid was centrifuged using the centrifugal machine (Beckman GS-6KR, Beckman Inc., U.S.A.) at 3500 rpm for 15 minutes to collect bacterial cell precipitation. The bacterial pellets were suspended in the fresh M9 medium 5 ml to prepare the test bacterial liquid.

EXAMPLE 1-(2)

Culture Condition of Test Microorganisms

EPEC strain was inoculated in LB agar plate and cultured at 37° C. for overnight (about 16 hours). One bacterial colony was inoculated to LB medium 3 ml and cultured at 37° C. for overnight without shaking. 0.5 ml was inoculated in to M9 medium 50 ml, and incubated at 37° C. for further 4 hours without shaking. Bacterial culture was centrifuged using the centrifugal machine (Beckman GS-6KR, Beckman Inc., U.S.A.) at 3500 rpm for 15 minutes to collect bacterial cell precipitation. The bacterial pellets were suspended in the fresh M9 medium 5 ml to prepare the test bacterial liquid.

EXAMPLE 2
Preparation of Erythrocytes Suspension

Rabbit red blood cells (obtainable from Nippon Biological Materials Center) 8 ml ware transferred into the 50 ml centrifugal tube, and PBS (0.8% NaCl, 0.02% KCl, 0.115% $Na_2HPO_4$ and 0.02% $KH_2PO_4$) 40 ml was added thereto and mixed gently. The mixture was centrifuged at 9° C. using centrifugal machine (Beckman GS-6KR, Beckman Inc., U.S.A.) at 2500 rpm for 5 minutes to obtain precipitated erythrocytes after removing off the supernatant. The precipitated erythrocytes were washed twice with PBS (0.8% NaCl, 0.02% KCl, 0.115% $Na_2HPO_4$ and 0.02% $KH_2PO_4$) 40 ml, centrifuged by the same manner as above to obtain the precipitated erythrocytes. Wet weight of precipitated erythrocytes obtained by centrifugation was measured, and the equal weight of M9 medium was added thereto and suspended the precipitated erythrocytes to obtain suspension of erythrocytes.

EXAMPLE 3
Preparation of Samples to be Evaluated

M9 medium 10 μl was previously added to each well of the 96 well microplate (3799, Coaster Inc., U.S.A.). A sample for evaluation 5 μl dissolved in purified water or methanol solution was added thereto and mixed well. In order to prevent drying of the sample for evaluation, the microplate was stored in a closed box covered with water wetted paper (Kimwipe, Kuresia Co., Japan) until adding the mixture of erythrocyte suspension and test bacterial cell solution.

EXAMPLE 4
Evaluation Using Microplate

Equivalent amount of the test bacterial solution [example 1-(1) or (2)] was added to the erythrocyte suspension prepared in example 2. The mixture, each 100 μl, was added to each well of the microplate, which contains the samples for evaluation prepared in example 3. Equivalent amount of M9 medium was added to the erythrocytes suspension 50 μl to prepare the negative control. Equivalent amount of the test bacterial solution [example 1-(1) or (2)] was added to the erythrocytes suspension 50 μl to prepare the positive control. The microplate was centrifuged (Beckman GS-6KR, Beckman Inc., U.S.A.) at 1500 rpm for 10 minutes in order to contact with the test bacterial solution and the erythrocytes suspension.

The microplate after the centrifugation was incubated at 37° C. for about 90 minutespBS (0.8% NaCl, 0.02% KCl, 0.115% $Na_2HPO_4$ and 0.02% $KH_2PO_4$) 150 μl was added to each well of the microplate, and gently suspended, then centrifuged (Beckman GS-6KR, Beckman Inc., U.S.A.) at 1500 rpm for 10 minutes at 9° C. Supernatant obtained by the centrifugation 100 μl was transferred into another microplate (3799, Coaster Inc., U.S.A.). Red color of hemoglobin appeared in the supernatant was measured at 550 nm by using microplate reader (Multiscan Plus MkII, Dainippon Seiyaku Co., Japan).

Inhibition rate of the sample for evaluation on the type III secretory mechanism is calculated by the following equation.

Inhibition rate (%)=100−[(A−B)/(C−B)×100]

wherein

A: data at 550 nm containing the sample for evaluation

B: data at 550 nm of negative control

C: data at 550 nm of positive control

EXAMPLE 5
Proof for Specificity of Detection Method on Type III Secretory Mechanism No inhibitory agent against type III secretory mechanism is found at present. Consequently, the present method for detection can not be proved by inhibitors for the type III secretory mechanism. However, the fact that whether the present detection method is specific to the type III secretory mechanism or nor can be proved by using the type III secretory mechanism lacking strain as a test organism. EPEC sepblacking strain having mutation on EPEC type III secretory mechanism is used as a test organism. Since the EPEC sepB lacking strain is mutated in the type III secretory mechanism, the type III secretory protein can not be released extracellularly.

EPEC sepB lacking strain, EPEC espA lacking strain, EPEC espB lacking strain and EPEC espD lacking strain were used as mutants of the type III secretory protein. These four lacking strains, i.e. sepB lacking strain, espA lacking strain, espBlacking strain and espD lacking strain, have no hemolytic activities (Infect. Immun., 67, 5538–5540, 1999). EPEC wild strain, EPEC sepB lacking strain, EPEC espA lacking strain, EPEC espB lacking strain and EPEC espD lacking strain are used as test organisms, and the hemolytic actions were generated according to the same procedures as in examples 1–4, and absorbancy at 550 nm was measured. The hemolytic activity of EPEC wild strain was set as 100% and percentage of the hemolytic activity of each lacking strain was calculated according to the equation hereinbefore. Results are shown in FIG. 25.

Figure 25:
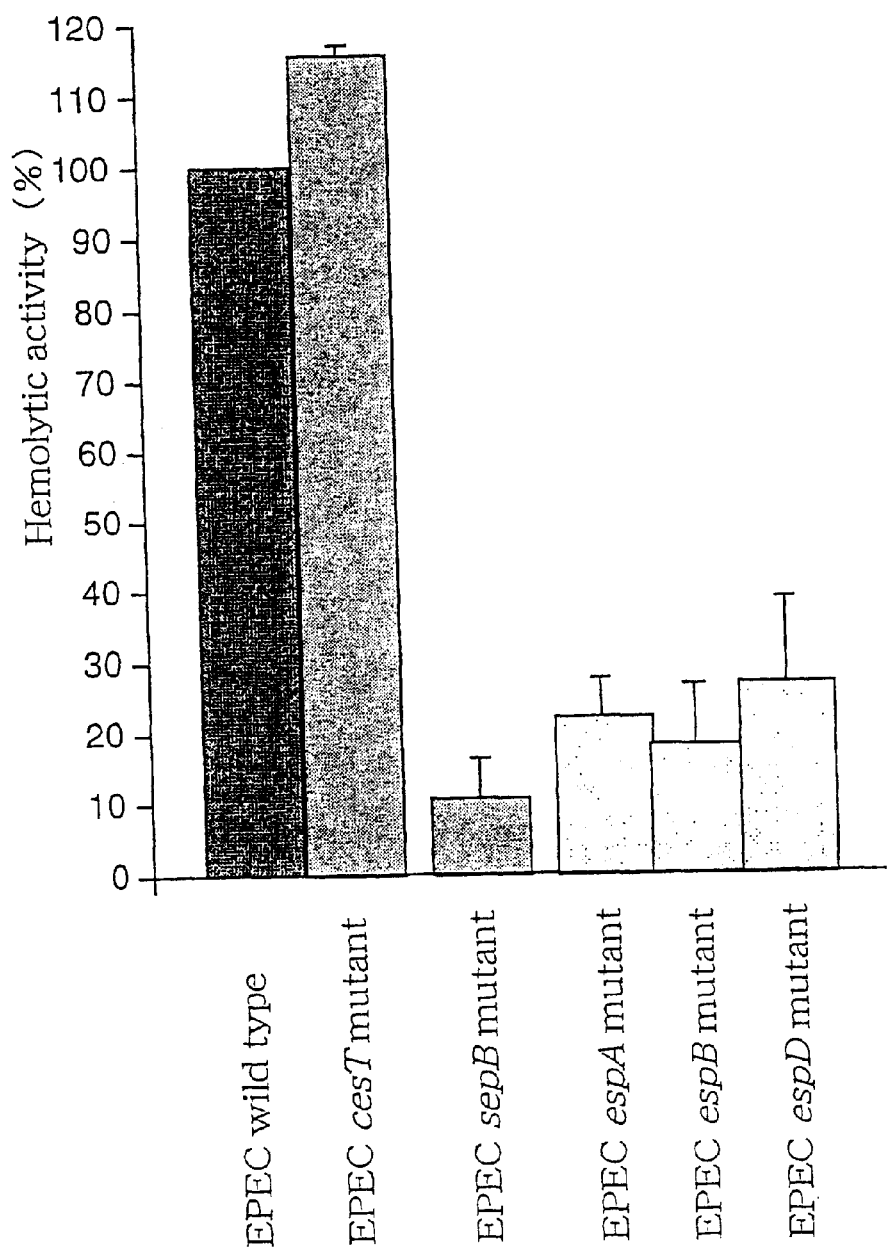
FIG. 25: Comparison with hemolytic activities (%) of EPEC wild strain and EPEC cesT defective strain, EPEC sepB defective strain, EPEC espA defective strain, EPEC espB defective strain and EPEC espD defective strain.

As demonstrated from the result in FIG. 25, the hemolytic activity of EPEC sepB lacking strain, which is a type III secretory mechanism lacking strain, shows significant decrease in the hemolytic activity as compared with that of EPEC wild strain. In mutant strains of the type III secretory protein, i.e. EPEC espA lacking strain, EPEC espB lacking strain and EPEC espD lacking strain, the hemolytic activities are extremely decreased as compared with EPEC wild strain. On the contrary, in EPEC cesT lacking strain, which is Tir specific chaperon without involving in the type III secretory mechanism, doesn't affect to the hemolytic activity as shown in FIG. 25.

As shown in the above, it is demonstrated that the hemolytic activity of the principle in the detective method of the present invention depends on the type III secretory mechanism and the type III secretory protein secreted therefrom.

In the present invention, EPEC cesT lacking strain is used in the test organism used for the hemolytic activity in the culturing method of example 1-(1). In EPEC cesT lacking strain, a Tir specific chaperon is defected and as a result, Tir is unstable and transfer of Tir to the host cell mediated by the type III secretory mechanism is decreased (Molecular Microbiol., 33, 1162–1175, 1999). Further, it is demonstrated from the result of the infectious experiments that Tir acts as a virulence factor (Infect. Immun., 68, 2171–2181, 2000). Consequently, EPEC cesT lacking strain, which has decreased intracellular transfer of Tir to host cells, is thought to have lower virulence as compared with EPEC wild strain. As a result, EPEC cesT lacking strain is thought to be preferably used as test organisms used in the present invention.

EXAMPLE 6

Proof for Effectiveness of the Present Method for Detection on Use of Test Bacteria not Only EPEC but Also Other Bacteria Having Type III Secretory Mechanism In the example 5, the present method for detection was shown that the method depends on the type III secretory mechanism and the type III secretory protein. However, the method of example 5 does not prove the effectiveness on use of bacteria having the type III secretory mechanism other than EPEC strains as test organisms. Consequently, test organisms having the type III secretory mechanism are selected from Shigella flexneri, Salmonella typhimuzium, Pseudomonas aeruginosa and Bordetella bronchiseptica and their hemolytic activities are tested. Since Bordetella bronchiseptica is slow growth in LB medium, the bacterial solution cultured for overnight in Stainer-Sholte medium is used for direct testing on the hemolytic activity.

Figure 26:
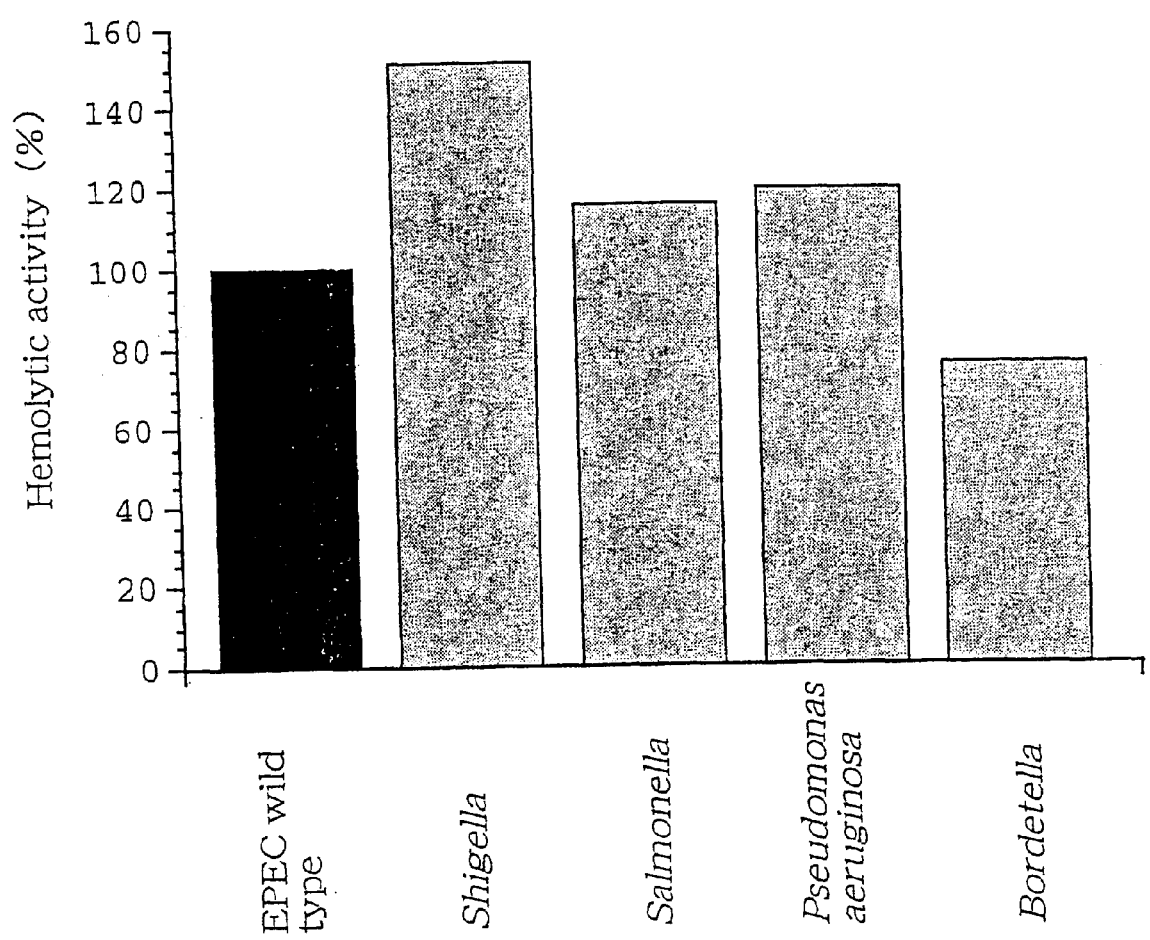
FIG. 26: Comparison with hemolytic activities of EPEC wild strain and other strains having type III secretion mechanism, i.e. Shigella, Salmonella, Pseudomonas and Bordetella. The hemolytic activity of EPEC wild strain is set as 100%.

In the hemolytic tests, the hemolytic activity was generated by the same procedure as in examples 1–4, and absorbancy at 550 nm was measured. Results are shown in FIG. 26. As obvious in FIG. 26, determining the hemolytic activities of each stain by indicating the hemolytic activity of EPEC wild strain as 100%, Shigella, Salmonella, Pseudomonas and Bordetella bronchiseptica show the hemolytic activity. As a result, the method for detection of the present invention can be used for not only EPEC wild strain but also other bacteria having the type III secretory mechanism.

EXAMPLE 7

A Proof for Type III Secretory Mechanism Depending on Hemolytic Activity Obtained by Using Different Bacteria In example 6, it has proven that test organisms including not only EPEC wild strain but also other bacteria having type III secretory mechanism could be used. However, the fact that whether the hemolytic activities obtained by using different bacteria in example 6 depend on the type III secretory mechanism is unknown. Consequently, lacking strains of the type III secretory mechanism and the type III secretory protein secreted therefrom in each strain of Shigella, Salmonella and Bordetella are used and the hemolytic activities are tested by the same hemolytic tests as in example 6, and results are compared with those of the parent strains. Results are shown in FIG. 27.

Figure 27:
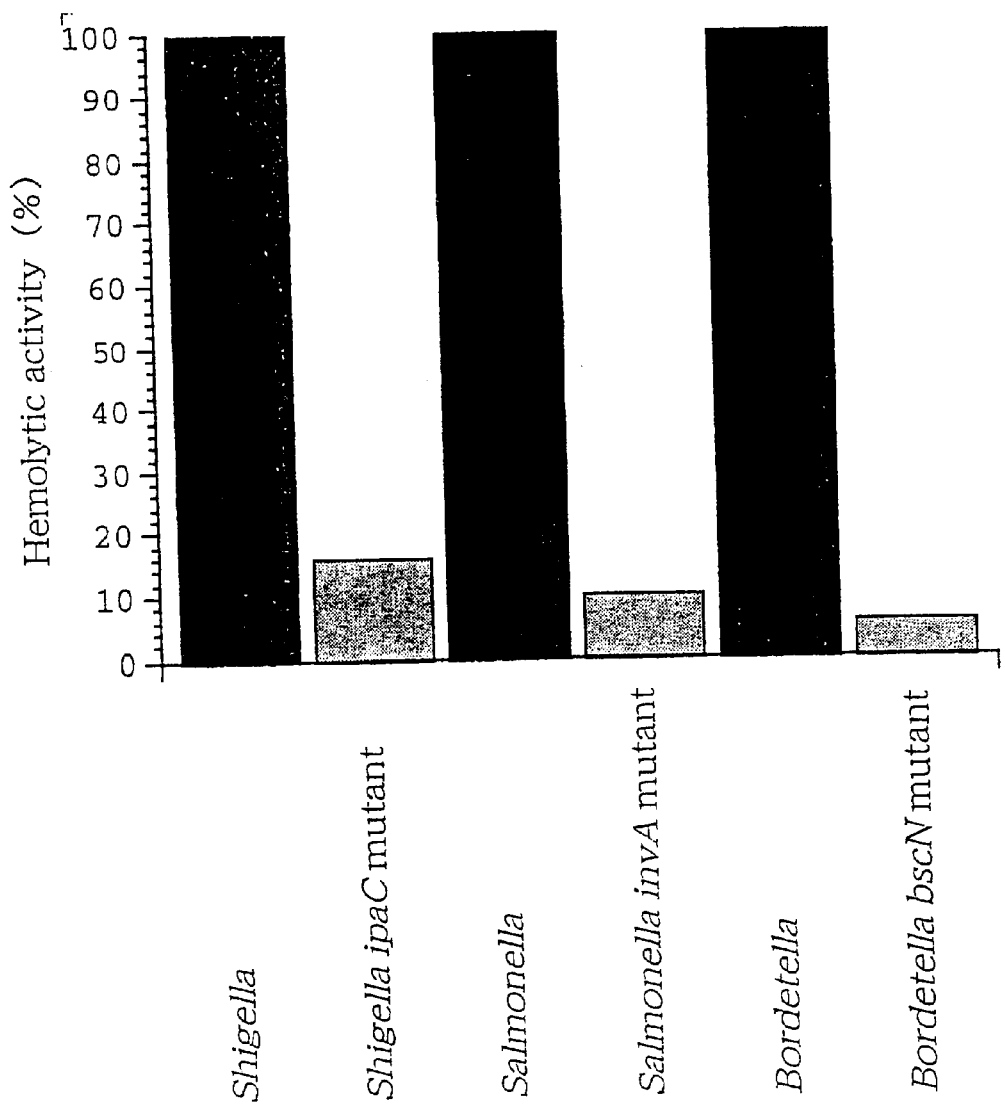
FIG. 27: Comparison with hemolytic activities in Shigella containing type III secretion mechanism vs. Shigella ipaC defective strain; Salmonella containing type III secretion mechanism vs. Salmonella invA defective strain; and Bordetella containing type III secretion mechanism vs. Bordetella bscN defective strain.

As shown in FIG. 27, when the activity of the parent strains of Shigella, Salmonella and Bordetella is set as 100%, the hemolytic activities of lacking strains of the type III secretory mechanism and the type III secretory protein are strongly inhibited. In Shigella type III secretory protein lacking strain, i.e. Shigella ipaC lacking strain, the hemolytic activity is significantly decreased. In Salmonella type III secretory mechanism lacking strain, i.e. Salmonella invA lacking strain, and Bordetella type III secretory mechanism lacking strain, i.e. Bordetella bscN lacking strain, the hemolytic activity is significantly decreased as same as in the above Shigella ipaC lacking strain. It is indicated that, in Salmonella, Shigella and Bordetella bronchiseptica, the hemolytic activity, which is a principle in the detection, depends on the type III secretory mechanism and the type III secretory protein thereof. As the results, the detection method of the present invention is not limited within EPEC type III secretory mechanism, and can be used for other bacteria having type III secretory mechanisms as test bacteria.

EXAMPLE 8

Evaluation of the Present Detection Method

As obvious from example 7, it is indicated that the present method for detection depends on the type III secretory mechanism and the type III secretory protein secreted therefrom, and that the test organism is not limited within EPEC. As described previously, the substance inhibiting type III secretory mechanism has not developed, since the effective detection method has not been developed so far. For that reason, antibiotics used at present are applied for the present detection method and evaluated.

Antibiotic used is tetracycline. Tetracycline inhibits bacterial protein synthesis by binding 30S subunit of bacterial ribosome. According to such protein synthesis inhibition, proteins constituting type III secretory mechanism can not be synthesized, and tetracycline is thought to inhibit the hemolytic activity mediated by the type III secretory mechanism.

Tetracycline 125 $\mu$g/ml in methanol solution was prepared and the detection methods from examples 1 to 5 were performed using this solution as samples for evaluation. EPEC cesT lacking strain was used as test organism, and a mixture of the bacterium and the erythrocyte suspension was prepared. Methanol solution of tetracycline was added at 5 $\mu$l per 100 $\mu$l of the mixture. The mixture was centrifuged for increased contact with erythrocytes and bacterial cells. After the centrifugation, the microplate was incubated at 37° C. for about 90 minutes. Inhibitory rate was calculated according to the method described in example 4.

Figure 28:
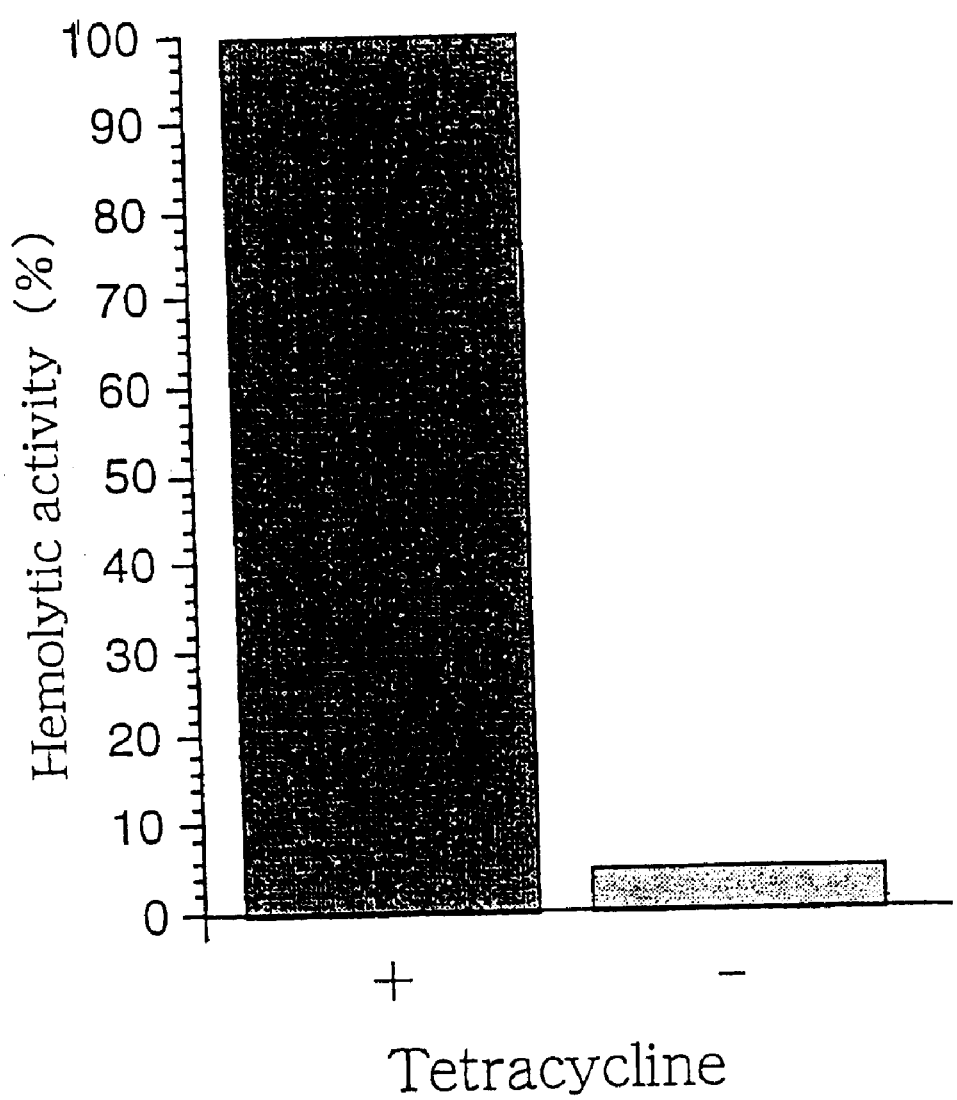
FIG. 28: Inhibitions of hemolytic activities with or without addition of antibiotic in test microorganisms.

The hemolytic activity of sample without adding tetracycline to the test organism is set to 100% and the hemolytic activity of the tetracycline added sample is shown in FIG. 28. As obvious from FIG. 28, tetracycline significantly inhibits the hemolytic activity. Further inhibition rate of tetracycline was calculated by the equation in example 4. Following result is obtained.

$$100-[(0.13-0.07)/(1.30\times0.07)\times100]=95.1\%$$

Even the final concentration of tetracycline in the reaction mixture is low concentration at 6 $\mu$g/ml, result for inhibiting the hemolytic activity about 100% could be obtained. As shown above, it was confirmed that addition of bacterial protein synthesis inhibitor results to inhibit significantly the hemolytic activity.

The result indicates that evaluation, test and detection of substances inhibiting functions of the type III secretory mechanism and the proteins secreted by the type III secretory mechanism can be possible. However, as described above, tetracycline has disadvantage of bactericidal action for the normal intestinal bacterial flora.

INDUSTRIAL APPLICABILITY

According to the present invention, the bacterial type III secretion mechanism and functions of the bacterial type III secretory proteins secreted therefrom can be treated within short time and large amounts thereof, without performing the animal infectious experiments, by exhibiting numerical index of the hemolytic activity of erythrocyte. Consequently, the present invention is useful for development of drugs and others.

What is claimed is:

1. A method for detection of a type III secretory mechanism inhibitor comprising mixing a bacterium having the type III secretory mechanism and an erythrocyte suspension, adding the type III secretory mechanism inhibitor thereto, and detecting changes in the thus formed hemolytic activity which indiates the effectiveness of a type III secretory mechanism inhibitor.

2. A method for detection of a substance inhibiting function of secretory protein of type III secretory mechanism comprising mixing a bacterium having the type III secretory mechanism and an erythrocyte suspension, adding the substance inhibiting the function of protein secreted by the type III secretory mechanism thereto, and detecting changes in the thus formed hemolytic activity which indicates the effectiveness of a substance inhibiting the function of type III secretory mechanism.

3. The method for detection according to claim 1 wherein the hemolytic activity generated in claim 1 is detected by colorimetry.

4. The method for detection according to claim 2 wherein the hemolytic activity generated in claim 2 is detected by colorimetry.

5. The method for detection according to claim 1 wherein bacteria is Salmonella, Pseudomonas, Shigella, Enteropathogenic *E. coli* and Bordetella.

6. The method for detection according to claim 2 wherein bacteria is Salmonella, Pseudomonas, Shigella, Enteropathogenic *E. coli* and Bordetella.

7. The method for detection according to claim 1, wherein Salmonella is *Salmonella typhimurium* SB147; Shigella is *Shigella flexneri* TK001; and Enteropathogenic *E. coli* is Enteropathogenic *Escherichia coli* cesT mutant, Enteropathogenic *Escherichia coli* sepB lacking strain, Enteropathogenic *Escherichia coli* espA lacking strain, Enteropathogenic *Escherichia coli* espB lacking strain and Enteropathogenic *Escherichia coli* espD lacking strain.

8. The method for detection according to claim 2, wherein Salmonella is *Salmonella typhimurium* SB147; Shigella is *Shigella flexneri* TK001; and Enteropathogenic *E. coli* is Enteropathogenic *Escherichia coli* cesT mutant, Enteropathogenic *Escherichia coli* sepB lacking strain, Enteropathogenic *Escherichia coli* espA lacking strain, Enteropathogenic *Escherichia coli* espB lacking strain and Enteropathogenic *Escherichia coli* espD lacking strain.

9. The method for detection according to claim 3, wherein Salmonella is *Salmonella typhimurium* SB147; Shigella is *Shigella flexneri* TK001; and Enteropathogenic *E. coli* is Enteropathogenic *Escherichia coli* cesT mutant, Enteropathogenic *Escherichia coli* sepB lacking strain, Enteropathogenic *Escherichia coli* espA lacking strain, Enteropathogenic *Escherichia coli* espB lacking strain and Enteropathogenic *Escherichia coli* espD lacking strain.

10. The method for detection according to claim 5, wherein Salmonella is *Salmonella typhimurium* SB147; Shigella is *Shigella flexneri* TK001; and Enteropathogenic *E. coli* is Enteropathogenic *Escherichia coli* cesT mutant, Enteropathogenic *Escherichia coli* sepB lacking strain, Enteropathogenic *Escherichia coli* espA lacking strain, Enteropathogenic *Escherichia coli* espB lacking strain and Enteropathogenic *Escherichia coli* espD lacking strain.

* * * * *